United States Patent
Mao et al.

(10) Patent No.: US 8,790,892 B2
(45) Date of Patent: Jul. 29, 2014

(54) SUBSTITUTED ANTHRAQUINONE DYES FOR CELLULAR STAINS AND ENZYME DETECTION

(75) Inventors: Fei Mao, Fremont, CA (US); Wai-Yee Leung, San Ramon, CA (US); Ching-Ying Cheung, San Ramon, CA (US); Lori Michelle Roberts, Belmont, CA (US)

(73) Assignee: Biotium, Inc., Hayward, CA (US)

( * ) Notice: Subject to any disclaimer, the term of this patent is extended or adjusted under 35 U.S.C. 154(b) by 0 days.

(21) Appl. No.: 13/439,821

(22) Filed: Apr. 4, 2012

(65) Prior Publication Data

US 2012/0252063 A1    Oct. 4, 2012

Related U.S. Application Data

(60) Provisional application No. 61/471,306, filed on Apr. 4, 2011.

(51) Int. Cl.
*G01N 1/30* (2006.01)

(52) U.S. Cl.
USPC .... 435/40.52; 435/40.5; 548/518; 548/300.4; 548/528; 552/218; 552/247

(58) Field of Classification Search
CPC ................ D06P 1/20; D06P 1/24; D06P 1/54
USPC ........... 435/40.52, 40.5; 548/518, 300.4, 528; 552/218, 247

See application file for complete search history.

(56) References Cited

U.S. PATENT DOCUMENTS

| | | |
|---|---|---|
| 6,468,753 B1 | 10/2002 | Smith et al. |
| 6,777,564 B2 | 8/2004 | Lee et al. |
| 7,060,427 B2 | 6/2006 | Smith et al. |
| 7,605,280 B2 | 10/2009 | Smith et al. |
| 2009/0047692 A1 | 2/2009 | Corry et al. |
| 2009/0148386 A1 | 6/2009 | Mao et al. |
| 2010/0062429 A1 | 3/2010 | Patton et al. |
| 2012/0028249 A1 | 2/2012 | Yue et al. |

FOREIGN PATENT DOCUMENTS

WO    WO 2011/124927 A1    10/2011

OTHER PUBLICATIONS

Interchim product information RedDot 1. Biotium. Revised Feb. 24, 2011.

International search report and written opinion dated Sep. 28, 2012 for PCT/US2012/032232.

Katzhendler, et al. Synthesis of aminoanthraquinone derivatives and their in vitro evaluation as potential anti-cancer drugs. European Journal of Medicinal Chemistry. 1989; 24:23-30.

*Primary Examiner* — Jason Sims
*Assistant Examiner* — Ibrahim D Bori
(74) *Attorney, Agent, or Firm* — Wilson Sonsini Goodrich & Rosati

(57) ABSTRACT

The invention discloses new substituted anthraquinone dyes that may be useful as cellular stains. In some aspect of the invention, the nuclear stains are useful for staining the nuclei of dead or fixed cells. Another aspect of the invention relates to substituted anthraquinone dyes comprising an enzyme substrate moiety that is transformable or cleavable by an enzyme such that the transformation or cleavage of the substrate moiety causes a detectable change in the functionality or spectral properties of the dye.

7 Claims, 7 Drawing Sheets b) 20 uM Dye No. 1 a) 5uM DRAQ5

Dye No. 7 + CF488A-phalloidin

Dye No. 7

SUBSTITUTED ANTHRAQUINONE DYES FOR CELLULAR STAINS AND ENZYME DETECTION

CROSS-REFERENCE

This application claims the benefit of U.S. Provisional Application Ser. No. 61/471,306, filed on Apr. 4, 2011, which is hereby incorporated by reference in its entirety.

BACKGROUND OF THE INVENTION

Fluorescent dyes are widely used in biological research and medical diagnostics. Fluorescent dyes are superior to conventional radioactive materials because fluorescent dyes are less expensive and less toxic, and can typically be detected with sufficient sensitivity. In particular, a diversity of fluorophores with a distinguishable color range has made it more practical to perform multiplexed assays capable of detecting multiple biological targets at the same time. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay.

Fluorescent nuclear stains are fluorescent dyes that can selectively stain the nuclei of cells. Nuclear stains may be divided into those that can cross cell membranes and those that cannot. Membrane permeable nuclear stains are useful for reveal the natural location of live cells and also for monitoring the nuclear changes during cell processes such as meiosis, mitosis and apoptosis. On the other hand, cell impermeant nuclear stains can be used to mark the nuclei of fixed cells or to selectively detect dead cells in the presence of live cells. Nuclear counterstains are particularly useful for immunofluorescence studies, where being able to fluorescently mark the nucleus of every single cell provides a means to analyze the immunostaining of sub-populations of cells relative to the entire cell population.

A number of fluorescent nuclear counterstains are commercially available. Examples of widely used nuclear counterstains include DAPI, Hoechst 33258, Hoechst 33342 and propidium iodide (PI) (Kenneth, H. J. and Douglas, A. K., Journal of Histochemistry and Cytochemistry 35, 123 (1987)). DAPI and the Hoechst dyes are UV-excitable blue fluorescent nucleic acid dyes. A major drawback of UV-excitable dyes is that relatively few confocal microscopes and other laser-based imaging instruments are equipped with UV excitation source. In addition, DAPI and the Hoechst dyes tend to have broad emission spectra that extend the fluorescent signal into the green and yellow detection channels, interfering with the detection of other fluorescent probes. PI has an absorption peak at ~530 nm and emission at ~610 nm. However, the 530 nm absorption peak of PI does not optimally match with the most common laser excitation wavelengths available. Furthermore, the 610 nm emission wavelength of PI is still not sufficiently long enough to separate from some of the orange and red fluorescent dyes widely used in immunofluorescence and other cellular staining. Various SYTO dyes from Invitrogen are available as nuclear counterstains for live cells (Bkaily et al., Mol. Cell. Biochem. 172, 171 (1997)). SYTO dyes have fluorescence wavelengths that occupy a spectral region otherwise more valuable to be reserved for other fluorescent probes in multiparameter imaging or detection. TOTO and YOYO dyes are membrane-impermeant nuclear stains. These are dimeric cyanine dyes carrying multiple positive charges for enhanced DNA-binding affinity. TOTO and YOYO dyes show high cytoplasmic background due to staining to RNA. Draq5 and Draq7, two DNA-binding dyes developed by Biostatus (U.S. Pat. Nos. 7,605,280; 7,060,427; and 6,468,753), are nuclear counterstains with far-red to near infrared fluorescence emission, which does not interfere with other detection channels in the visible spectral region useful for other probes. See also US Patent Application 2010/0062429. However, for fixed cells, the nuclear specificity of both Drq5 and Draq7 suffers, which poses problems for their application in immunofluorescence staining, where cell fixation and permeabilization is routine practice.

Thus, there remains a need for alternate fluorescent nuclear stains.

SUMMARY OF THE INVENTION

In various embodiments, a substituted anthraquinone dye is provided having the following general structure:

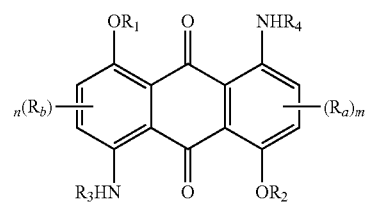

Formula 1 wherein
$R_a$ and $R_b$ are independently H, methyl, methoxy or a halogen;
m and n are independently 0, 1, or 2;
$R_1$ and $R_2$ are independently H or an enzyme substrate moiety, or a substituent that together with the oxygen atom to which it is attached forms an enzyme substrate moiety;
$R_3$ and $R_4$ are independently H, methyl, an enzyme substrate moiety, a substituent that together with the nitrogen atom to which it is attached forms an enzyme substrate moiety, formyl, acetyl, an alkanoyl having the formula of Formula 2, or an alkyl having the formula of Formula 3:

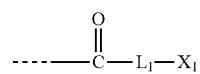

Formula 2

Formula 3 where $L_1$ is a link comprising 2-12 non-hydrogen atoms;
$X_1$ is a substituent selected from the group consisting of a substituted or unsubstituted amino, a substituted or unsubstituted amidino, a substituted or unsubstituted guanidino, a substituted or unsubstituted aminooxy, a substituted or unsubstituted hydroxylamino, a substituted or unsubstituted hydrazino, a $C_{3-6}$ trialkylammonium, a substituted or unsubstituted, natural or unnatural amino acid with a free alpha- or beta-amine where the amino acid is attached to $L_1$ via an amide bond;
$L_2$ is a link comprising 2-12 non-hydrogen atoms;

$X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond; or $X_2$ is a mono- or disubstituted amino where the mono- or di-substituents and $L_2$ and the nitrogen atom to which they are attached form at least one 3-7 membered saturated ring; or $X_2$ is a substituted or unsubstituted amino and $L_2$ comprises at least one moiety selected from the group consisting of an ether bond, an amide bond, a hydroxy and a saturated 3-7 membered ring.

In some embodiments, $R_a$ and $R_b$ are both H and n=m=2; or $R_1$ and $R_2$ are both H, and at least one of $R_3$ and $R_4$ is an alkanoyl according to Formula 2. In various embodiments, the compound is selected from Table 1 or Table 2.

In some embodiments, at least one of $R_3$ and $R_4$ is an alkyl according to Formula 3,

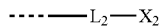

wherein $L_2$ is a link comprising 2-12 non-hydrogen atoms;
$X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond; or $X_2$ is a mono- or disubstituted amino where the mono- or di-substituents and $L_2$ and the nitrogen atom to which they are attached form at least one 3-7 membered saturated ring; or $X_2$ is a substituted or unsubstituted amino and $L_2$ comprises at least one moiety selected from the group consisting of an ether bond, an amide bond, a hydroxy and a saturated 3-7 membered ring.

In various embodiments, $L_2$ comprises 2-12 nonhydrogen atoms, for example 2-12 atoms selected from C, N, and O. In some embodiments, $L_2$ is $C_2$-$C_{12}$ alkylene, for example ethylene.

In some embodiments, $X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond. For example, $X_2$ is substituted or unsubstituted amidino or substituted or unsubstituted guanidino. In some embodiments, $X_2$ is unsubstituted amidino. In other embodiments, $X_2$ is unsubstituted guanidino.

In some embodiments, at least one of $R_3$ and $R_4$ has the Formula 3a, 3b, 3c or 3d:

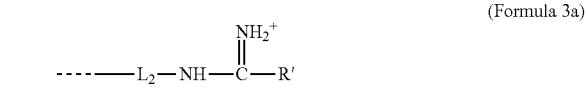
(Formula 3a)

(Formula 3b)

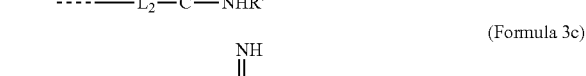
(Formula 3c)

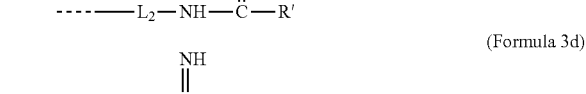
(Formula 3d)

wherein R' is H or alkyl.

In one embodiment, the dye is:

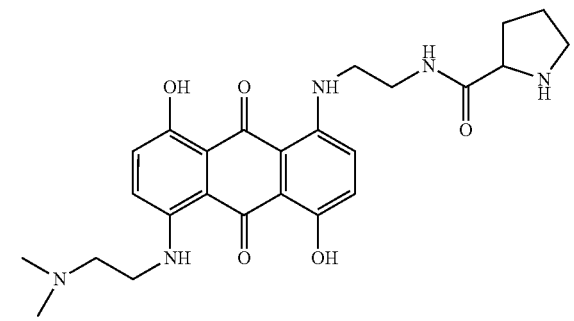 [SMILES: CN(C)CCNc1ccc(O)c2c1C(=O)c1c(O)ccc(NCCNC(=O)C3CCCN3)c1C2=O]

Further provided herein are substituted anthraquinone dyes of Formula 5:

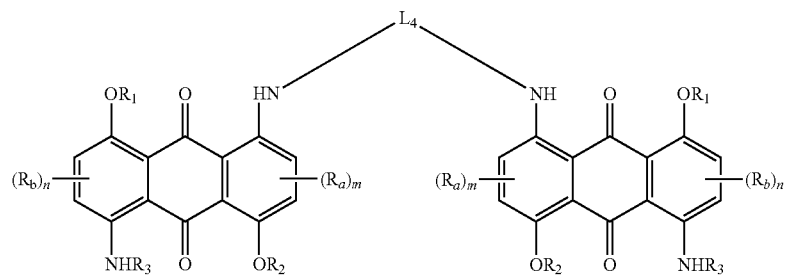

wherein:
each $R_a$ and $R_b$ is independently H, methyl, methoxy or a halogen;
each m and n is independently 0, 1, or 2;
each $R_1$ and $R_2$ is independently H or an enzyme substrate moiety, or a substituent that together with the oxygen atom to which it is attached forms an enzyme substrate moiety;
each $R_3$ is independently H, methyl, an enzyme substrate moiety, a substituent that together with the nitrogen atom to which it is attached forms an enzyme substrate moiety, formyl, acetyl, an alkanoyl having the formula of Formula 2, or an alkyl having the formula of Formula 3:

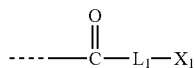

Formula 2

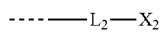

Formula 3

$L_1$ is a link comprising 2-12 non-hydrogen atoms;
$X_1$ is a substituent selected from the group consisting of a substituted or unsubstituted amino, a substituted or unsubstituted amidino, a substituted or unsubstituted guanidino, a substituted or unsubstituted aminooxy, a substituted or unsubstituted hydroxylamino, a substituted or unsubstituted hydrazino, a $C_{3-6}$ trialkylammonium, a substituted or unsubstituted, natural or unnatural amino acid with a free alpha- or beta-amine where the amino acid is attached to $L_1$ via an amide bond;
$L_2$ is a link comprising 2-12 non-hydrogen atoms;
$X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid where the amino acid is attached to $L_2$ via an amide bond; or $X_2$ is a mono-, di- or trisubstituted amino group;
$L_4$ is

-$L_2$-$X_2'$-$L_2'$-$X_2''$-$L_2''$-, wherein $L_2$, $L_2'$, and $L_2''$ are independently links comprising 2-12 non-carbon atoms; and
$X_2'$ and $X_2''$ are independently selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond; or $X_2$ is a mono-, di- or trisubstituted amino group.

In some embodiments, each $L_2$, $L_2'$, and $L_2''$ is independently $C_2$-$C_{12}$ alkylene, for example methylene or ethylene. For example, $L_2$ and $L_2''$ are ethylene. In some embodiments, $X_2'$ and $X_2''$ are amidino.

In some embodiments, the dye is:

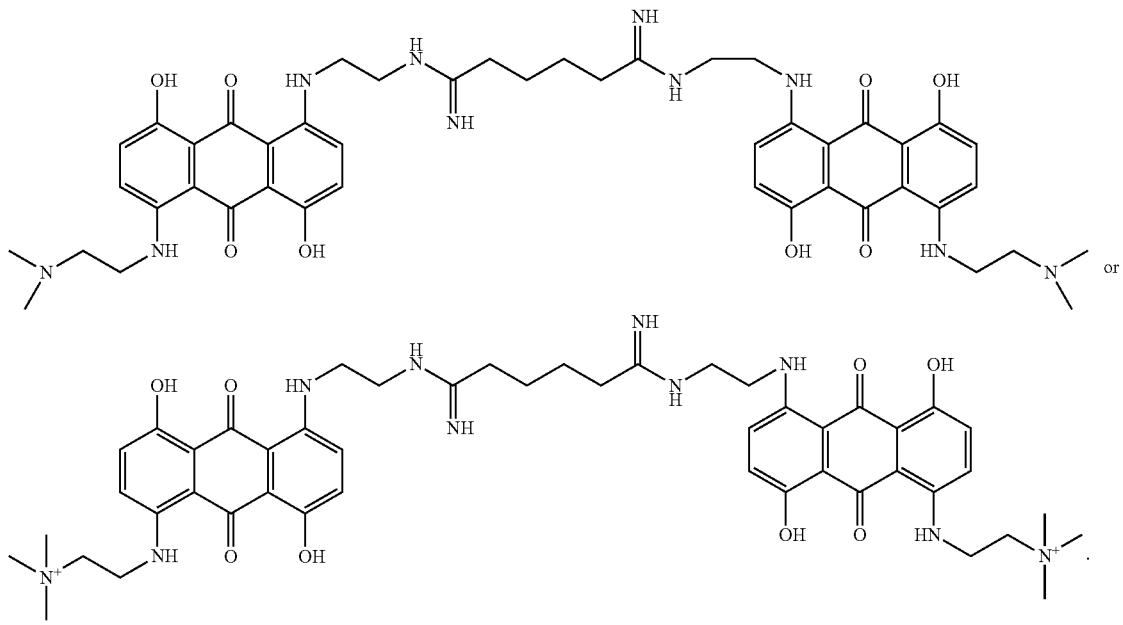

In various embodiments, compounds disclosed herein comprise at least one enzyme substrate moiety wherein the transformation of the substrate moiety by an enzyme causes a detectable change in ether the spectral property or functionality of the anthraquinone dye. For example, an anthraquinone dye may comprise an enzyme substrate moiety according to the general structure of Formula 4:

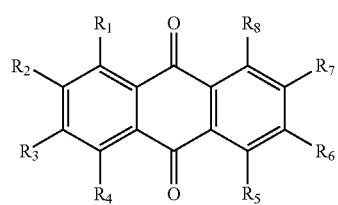

Formula 4 wherein at least one of $R_1$-$R_8$ is an enzyme substrate moiety or a substituent comprising an enzyme substrate moiety, wherein following enzymatic cleavage said substrate moiety or substituent comprising a substrate moiety results in a substituent selected from the group consisting of —OH, —$NH_2$, —NH-$L_3$-OH, and —NH-$L_3$-$NH_2$, where $L_3$ is a linker group.

Also disclosed herein are methods for staining a biological sample comprising incubating a biological sample and an anthraquinone dye of Formula 1 or Formula 4. In general, the anthraquinone comprises an enzyme substrate moiety, the biological sample comprises live cells or active enzyme. When the anthraquinone does not comprise an enzyme substrate moiety, the biological sample may comprise live cells, fixed cells or fixed and permeabilized cells. In various embodiments, a method as disclosed herein of analyzing a biological sample comprising cells comprises the steps of: i) incubating said biological sample in a biological buffer in the presence of an anthraquinone dye of Formula 1 or Formula 4 for a time sufficient to cause staining; ii) illuminating the stained sample with a light source sufficient to excite the dye; and iii) detecting the emitted fluorescence from the sample using a suitable instrument.

In addition, methods are disclosed for detecting enzyme activity, the method comprising the steps of: i) incubating a biological sample comprising or thought to comprise an active enzyme in a biological buffer in the presence of an anthraquinone dye of Formula 1 or Formula 4 comprising an enzyme substrate moiety specific for said enzyme to be detected for at least 5 minutes; ii) illuminating the treated sample with a light source sufficient to excite the enzymatically produced dye product; and iii) detecting the emitted fluorescence from the sample using a suitable instrument.

Further provided herein are kits comprising a substituted anthraquinone dye and instructions for use of said substituted anthraquinone dye.

INCORPORATION BY REFERENCE

All publications, patents, and patent applications mentioned in this specification are herein incorporated by reference to the same extent as if each individual publication, patent, or patent application was specifically and individually indicated to be incorporated by reference. The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)), each of which are incorporated by reference for their teachings of conventional techniques.

Throughout the present disclosure, dye functionality means the cellular staining pattern of the dye. Anthraquinone dyes having specific cellular staining pattern have been disclosed in US Patent Application No. 2010/0062429 A1 and U.S. Pat. Nos. 7,605,280 and 7,060,427. For example, US patent application No. 2010/0062429 disclosed various anthraquinone dyes having different cellular staining specificity, including the stainings of mitochondria, Golgi, vacuoles, lysosomes, cell nuclei and entire cells. U.S. Pat. Nos. 7,605,280 and 7,060,427 disclose anthraquinone dyes that specifically stain cell nuclei.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
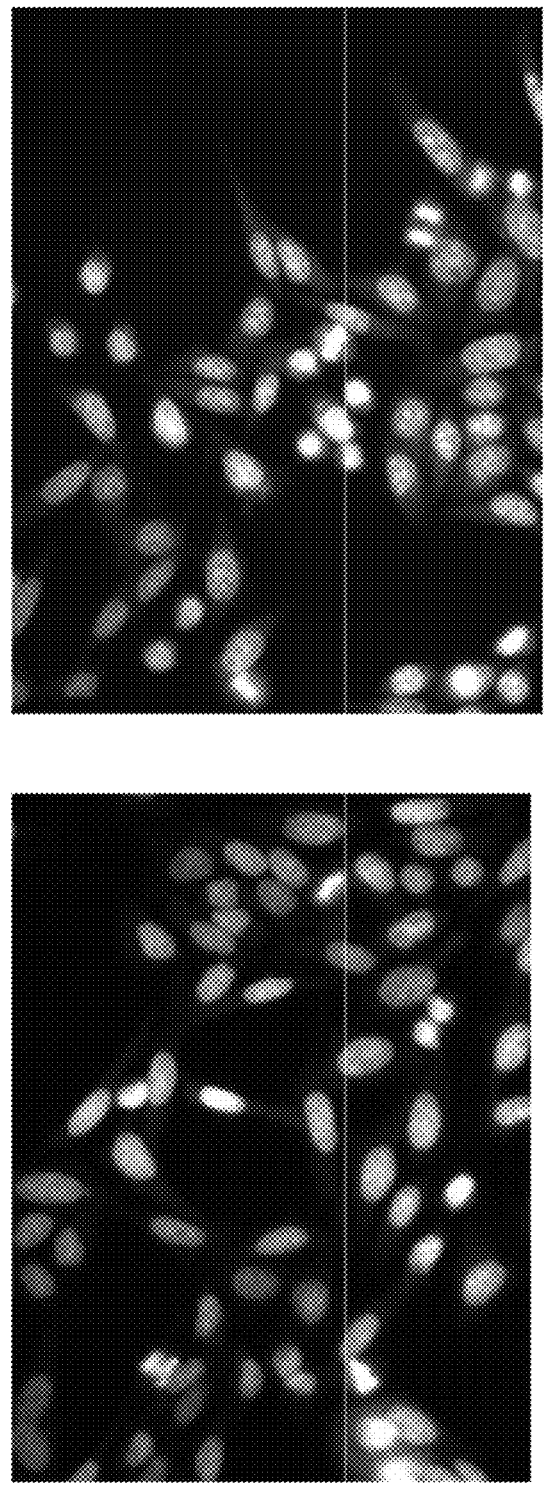
FIG. 1 shows staining of live cells. The figure shows fluorescent microscopic images of HeLa cells stained with a) Draq5 and b) Dye No. 1, respectively. The results show that, like Draq5, Dye No. 1 stained the nuclei of live cells specifically.

The invention discloses new substituted anthraquinone dyes that may be useful as cellular stains. According to one embodiment, the substituted anthraquinones are directly useful as cell nuclear stains. In some cases, the nuclear stains are cell membrane-permeant and therefore can be used to stain the nuclei of both live and dead cells. In some aspect of the invention, the nuclear stains are cell membrane-impermeant and thus are useful for staining the nuclei of dead or fixed cells. According to an aspect of the invention, cell-permeant nuclear stains of the invention are less toxic to live cells than Draq5. According to another aspect of the invention, cell-impermeant nuclear stains of the invention show less background staining than Draq7.

Another aspect of the invention relates to substituted anthraquinone dyes comprising an enzyme substrate moiety that is transformable or cleavable by an enzyme such that the transformation or cleavage of the substrate moiety causes a detectable change in the functionality or spectral properties of the dye.

Compounds

According to one embodiment, substituted anthraquinone dyes have the following general structure:

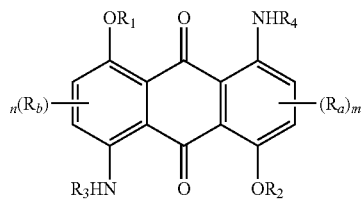

Formula 1 wherein
$R_a$ and $R_b$ are independently H, methyl, methoxy or a halogen;
m and n are independently 0, 1, and 2;
$R_1$ and $R_2$ are independently H or an enzyme substrate moiety, or a substituent that together with the oxygen atom to which it is attached forms an enzyme substrate moiety;
$R_3$ and $R_4$ are independently H, methyl, an enzyme substrate moiety, a substituent that together with the nitrogen atom to which it is attached forms an enzyme substrate moiety, formyl, acetyl, or an alkanoyl having the formula of Formula 2:

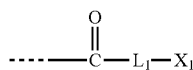

Formula 2 where $L_1$ is a link comprising 2-12 non-hydrogen atoms; and $X_1$ is a substituent selected from the group consisting of a substituted or unsubstituted amino, a substituted or unsubstituted amidino, a substituted or unsubstituted guanidino, a substituted or unsubstituted aminooxy, a substituted or unsubstituted hydroxylamino, a substituted or unsubstituted hydrazino, a $C_{3-6}$ trialkylammonium, a substituted or unsubstituted, natural or unnatural amino acid with a free alpha- or beta-amine where the amino acid is attached to $L_1$ via an amide bond.

It should be readily understood to one skilled in the art that when $X_1$ is an amidino, the amidino may be covalently linked to $L_1$ either via one of the two nitrogen atoms or the carbon atom of the amidino, as illustrated below:

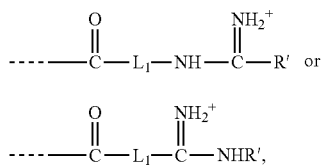

Formula 2a

Formula 2b where in both Formula 2a and Formula 2b, R' is H (i.e., unsubstituted) or an alkyl (i.e., substituted). When not specifically mentioned which way said amidino is connected to $L_1$, it is implied that either way is acceptable.

Alternatively, $R_3$ or $R_4$ is independently an alkyl having the formula of Formula 3:

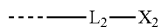

Formula 3 wherein $L_2$ is a link comprising 2-12 non-hydrogen atoms and $X_2$ is a substituent selected from the group consisting of a substituted or unsubstituted amino, a substituted or unsubstituted amidino (as described for Formula 2), a substituted or unsubstituted guanidino, a substituted or unsubstituted aminooxy, a substituted or unsubstituted hydroxylamino, a substituted or unsubstituted hydrazino, a $C_{2-6}$ trialkylammonium, a substituted or unsubstituted, natural or unnatural amino acid with a free alpha- or beta-amine where the amino acid is attached to $L_2$ via an amide bond.

Likewise, when $X_2$ is an amidino, the amidino may be covalently linked to $L_2$ either via one of the two nitrogen atoms or the carbon atom of the amidino, as illustrated below:

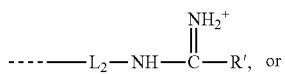

Formual 3a

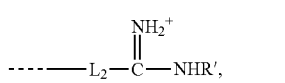

Formual 3b where in both Formula 3a and Formula 3b, R' is H (i.e., unsubstituted) or an alkyl (i.e., substituted). When not specifically mentioned which way said amidino is connected to $L_2$, it is implied that either way is acceptable.

In various embodiments of Formula 3, when $X_2$ is a mono- or disubstituted amino, the mono- or di-substituents and $L_2$ and the nitrogen atom to which they are attached form at least one 3-7 membered saturated ring. In some embodiments, the ring is a saturated bicyclo ring. For example, the ring may be as shown in Dye No. 12 of Table 1. In some embodiments, $X_2$ is a substituted or unsubstituted amino and $L_2$ comprises at least one moiety selected from the group consisting of an ether bond, an amide bond, a hydroxy and a saturated 3-7 membered ring.

In various embodiments, an anthraquinone dye according to Formula 1 meets at least one of the following conditions:
1) the dye comprises at least one enzyme substrate moiety as described herein;
2) at least one of $R_3$ or $R_4$ is formyl, acetyl, or an alkanoyl according to Formula 2; or
3) at least one of $R_3$ and $R_4$ is an alkyl according to Formula 3, where $X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond; or $X_2$ is a mono- or disubstituted amino where the mono- or di-substituents and $L_2$ and the nitrogen atom to which they are attached form at least one 3-7 membered saturated ring; or $X_2$ is a substituted or unsubstituted amino and $L_2$ comprises at least one moiety selected from the group consisting of an ether bond, an amide bond, a hydroxy and a saturated 3-7 membered ring.

In any embodiments where $X_2$ is a mono-, di-, or tri-substituted amino group, the designation of the degree of substitution (e.g. "mono-", "di-", or "tri-") refers to the number of groups in addition to $L_2$ substituted on the amino group. For example, an $X_2$ which is a "mono-substituted" amino group is understood to be substituted by $L_2$ and additionally by another non-hydrogen substituent (for example a methyl group).

According to various embodiments, $R_a$ and $R_b$ are both H and n=m=2.

According to one embodiment, $R_1$ and $R_2$ are both H, and at least one of $R_3$ and $R_4$ is an alkanoyl according to Formula 2. More preferably, the alkanoyl is according to Formula 2 where $X_1$ is selected from the group consisting of a substituted or unsubstituted amino, a substituted or unsubstituted amidino, a substituted or unsubstituted guanidino, a $C_{2-6}$ trialkylammonium, a substituted or unsubstituted, natural or unnatural amino acid with a free alpha- or beta-amine where the amino acid is attached to $L_2$ via an amide bond. In various embodiments, $X_1$ is selected from a substituted or unsubstituted amino, a substituted or unsubstituted amidino, and a substituted or unsubstituted guanidine. According to some embodiments, $R_1$ and $R_2$ are the same.

In another preferred embodiment, $R_1$ and $R_2$ are both H, and at least one of $R_3$ and $R_4$ is an alkyl according to Formula 3, where $L_2$ is a $C_{2-3}$ alkylene and $X_2$ is selected from the group consisting of a substituted or unsubstituted amidino, a substituted or unsubstituted guanidino, and a substituted or unsubstituted, natural or unnatural amino acid with a free alpha- or beta-amine where the amino acid is attached to $L_2$ via an amide bond. When $X_2$ is an amino acid, the amino acid is preferably L- or D-proline, L- or D-glycine, L- or D-lysine or L- or D-arginine.

According to one preferred embodiment, $R_1$ and $R_2$ are both H, and $R_3$ and $R_4$ are the same and are both an alkyl according to Formula 3, where $L_2$ is $C_{2-4}$ alkylene and $X_2$ is a substituted or unsubstituted amidino, or a substituted or unsubstituted guanidine.

According to yet another preferred embodiment of the invention, both $R_1$ and $R_2$ are H, $R_3$ is an alkyl according to Formula 3 where $X_2$ is a $C_{2-4}$ dialkylamino, and $R_4$ is an alkyl comprising a substituted amidino according to Formula 3a. According to one embodiment, the R' substituent of the amidino is an alkyl comprising another nucleic acid-binding dye. Thus, the resulting dye is a dimeric nucleic acid-binding dye. According to a preferred embodiment, R' is a linker molecule covalently connecting two identical anthraquinone dye molecules according to Formula 1. Examples of such dimeric anthraquinone dyes comprising two amidino moieties are Dye No. 7 and Dye No. 9 of Table 1.

Some preferred nuclear staining anthraquinone dyes according to the invention are listed in Table 1.

TABLE 1

List of Formula 1-based anthraquinone nuclear stains*

| Dye No. | Structure | Description of required $R_3$ or $R_4$ |
|---|---|---|
| 1 | 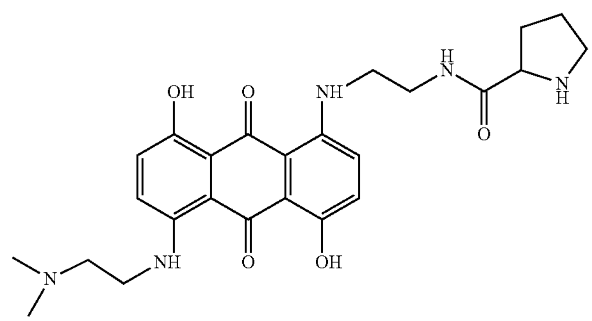 [SMILES: CN(C)CCNc1ccc(O)c2c1C(=O)c1c(O)ccc(NCCNC(=O)C3CCCN3)c1C2=O] | Alkyl comprising an amino acid (proline) |
| 2 | 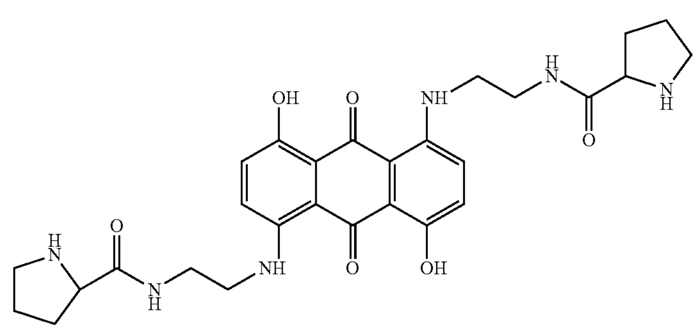 [SMILES: O=C1c2c(O)ccc(NCCNC(=O)C3CCCN3)c2C(=O)c2c(O)ccc(NCCNC(=O)C3CCCN3)c21] | Alkyl comprising an amino acid (proline) |

TABLE 1-continued

List of Formula 1-based anthraquinone nuclear stains*

| Dye No. | Structure | Description of required $R_3$ or $R_4$ |
|---|---|---|
| 3 | 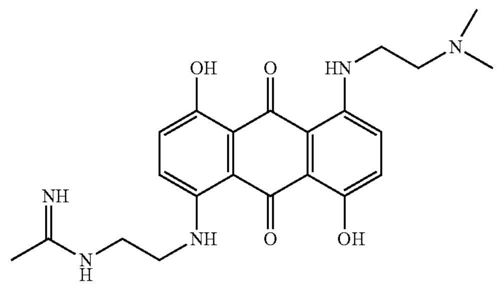 [SMILES: CC(=N)NCCNc1ccc(O)c2c1C(=O)c1c(O)ccc(NCCN(C)C)c1C2=O] | Alkyl comprising substituted amidine |
| 4 | 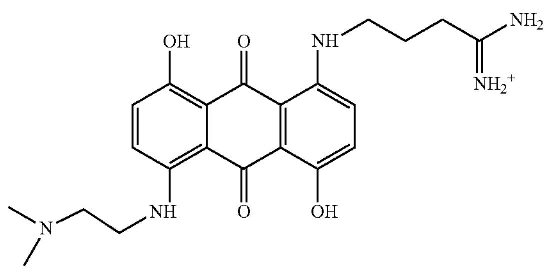 [SMILES: CN(C)CCNc1ccc(O)c2c1C(=O)c1c(O)ccc(NCCCC(N)=[NH2+])c1C2=O] | Alkyl comprising amidine |
| 5 | 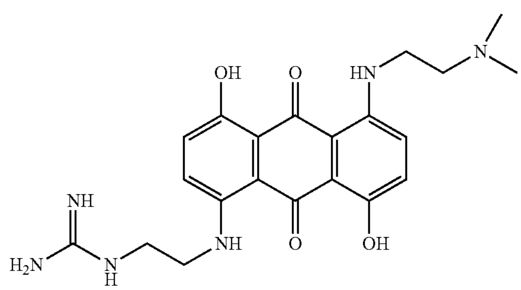 [SMILES: CN(C)CCNc1ccc(O)c2c1C(=O)c1c(O)ccc(NCCNC(=N)N)c1C2=O] | Alkyl comprising guanidine |
| 6 | 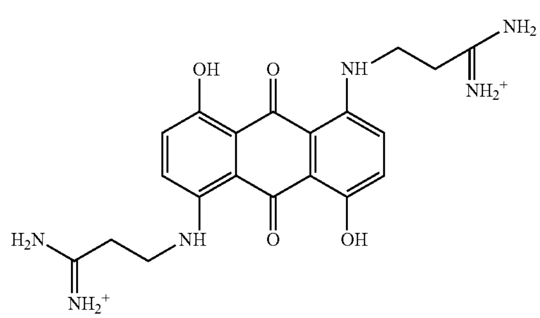 [SMILES: NC(=[NH2+])CCNc1ccc(O)c2c1C(=O)c1c(O)ccc(NCCC(N)=[NH2+])c1C2=O] | Alkyl comprising amidine |
| 7 | 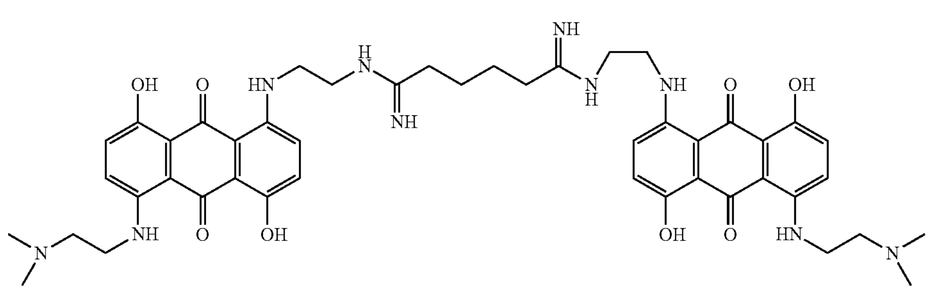 | Alkyl comprising amidine (dimeric) |

TABLE 1-continued
List of Formula 1-based anthraquinone nuclear stains*
| Dye No. | Structure | Description of required $R_3$ or $R_4$ |
|---|---|---|
| 8 | 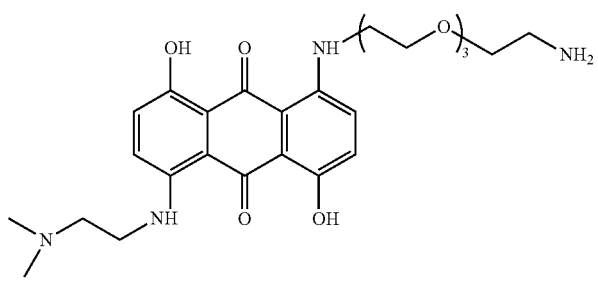 | Alkyl of Formula 3 |
| 9 | 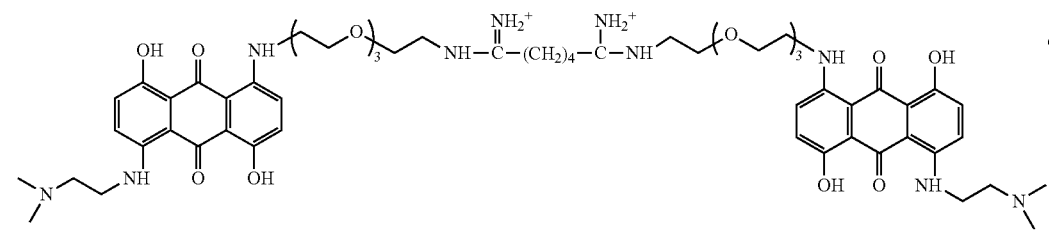 | Alkyl comprising amidine (dimeric) |
| 10 | 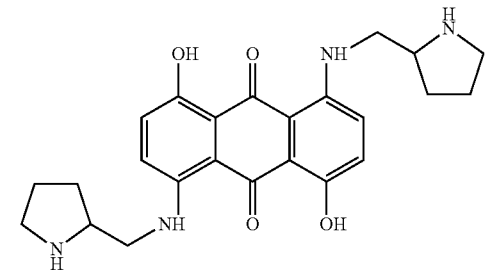 [SMILES: O=C1c2c(O)ccc(NCC3CCCN3)c2C(=O)c2c(O)ccc(NCC3CCCN3)c21] | Alkyl of Formula 3 |
| 11 | 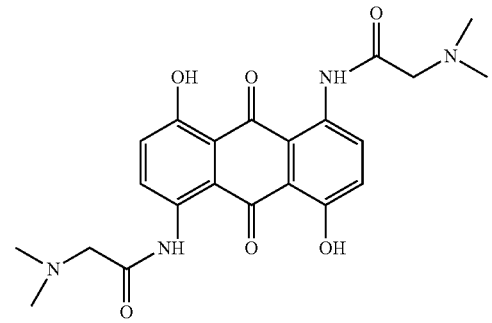 | Alkanoyl comprising substituted amine |
| 12 | 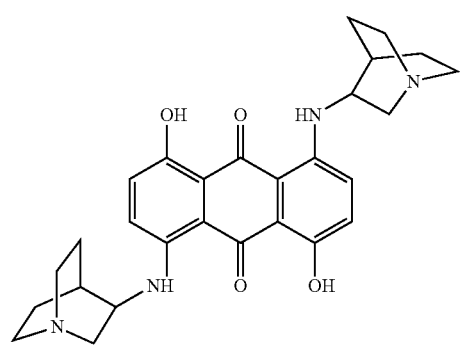 [SMILES: O=C1c2c(O)ccc(NC3CN4CCC3CC4)c2C(=O)c2c(O)ccc(NC3CN4CCC3CC4)c21] | Alkyl of Formula 3 |

TABLE 1-continued

List of Formula 1-based anthraquinone nuclear stains*

| Dye No. | Structure | Description of required $R_3$ or $R_4$ |
|---|---|---|
| 13 | 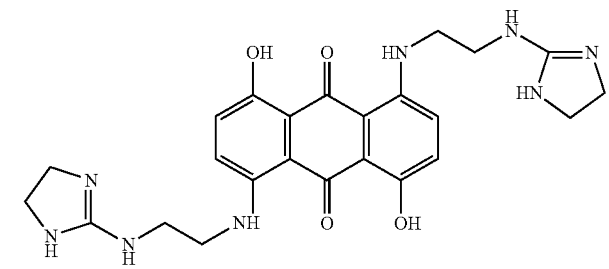 [SMILES: O=C1c2c(O)ccc(NCCNC3=NCCN3)c2C(=O)c2c(O)ccc(NCCNC3=NCCN3)c21] | Alkyl comprising substituted guanidine |
| 14 | 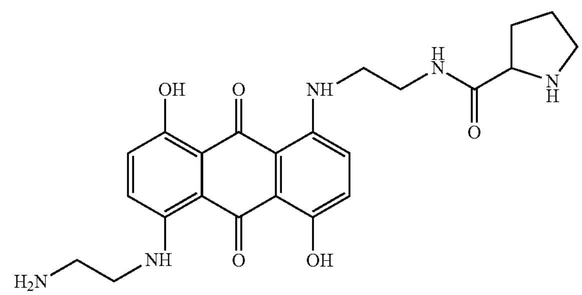 [SMILES: NCCNc1ccc(O)c2c1C(=O)c1c(O)ccc(NCCNC(=O)C3CCCN3)c1C2=O] | Alkyl comprising an amino acid (proline) |
| 15 | 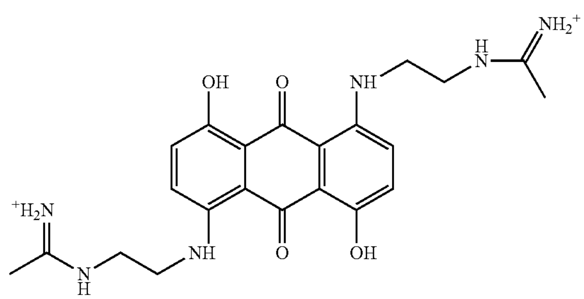 [SMILES: CC(=[NH2+])NCCNc1ccc(O)c2c1C(=O)c1c(O)ccc(NCCNC(C)=[NH2+])c1C2=O] | Alkyl comprising amidine |
| 16 | 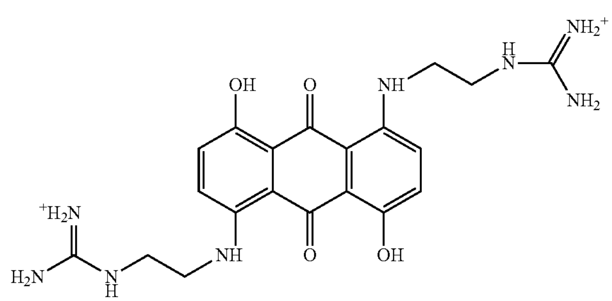 [SMILES: NC(=[NH2+])NCCNc1ccc(O)c2c1C(=O)c1c(O)ccc(NCCNC(N)=[NH2+])c1C2=O] | Alkyl comprising guanidine |
| 17 | 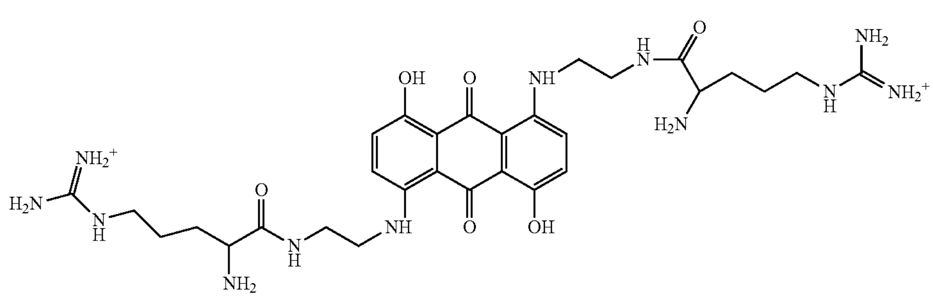 [SMILES: NC(=[NH2+])NCCCC(N)C(=O)NCCNc1ccc(O)c2c1C(=O)c1c(O)ccc(NCCNC(=O)C(N)CCCNC(N)=[NH2+])c1C2=O] | Alkyl comprising an amino acid (arginine) |

TABLE 1-continued

List of Formula 1-based anthraquinone nuclear stains*

| Dye No. | Structure | Description of required $R_3$ or $R_4$ |
|---|---|---|
| 25 | 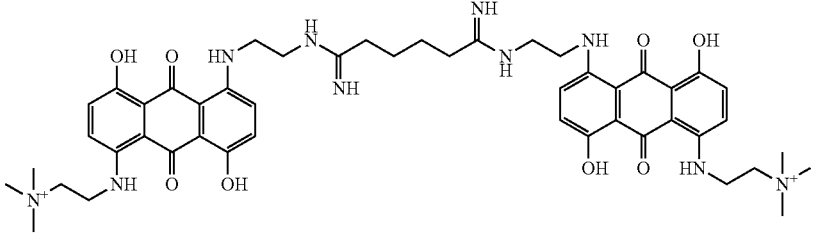 | Alkyl comprising amidine (dimeric) |

*for simplicity, any counter ion necessary for balancing the charge of the dye is omitted.

In various embodiments, the $X_1$ and $X_2$ in Formulas 1 and 2 are either partially, substantially or fully positively charged moieties under physiological conditions. Positively charged groups enhance nucleic acid binding affinity of the dyes by facilitating the electrostatic interaction between the positively charged group and phosphate groups of nucleic acids. Primary, secondary and tertiary amino groups are generally partially positively charged while amidino, guanidino, hydrazino and hydroxyamino and aminooxy are substantially positively charged. On the other hand, trialkylammonium groups are fully positively charged groups.

Where the anthraquinone dye of the invention is a charged moiety, the dye may be associated with one or more counter ions which balance the charge of the dye. When the anthraquinone dye is positively charged, a suitable counter ion can be an anion, for instance a biologically compatible anion. Biologically compatible anions include, but are not limited to, halides (such as chloride, fluoride, iodide or bromide), sulfate, phosphate, acetate, trifluoroacetate, lactate, citrate, gluconate, or hydroxyethansulfate. When depicting a formula of an anthraquinone dye of the invention, the counter ion may or may not be explicitly described for simplicity, even though it can be present as understood by a person skilled in the art.

While not wishing to be bound by theory, it is believed that anthraquinone dyes of the invention that are neutral or partially positively charged can easily cross cell membranes and thus are useful for staining live cells. In contrast, anthraquinone dyes of the invention that are substantially or highly positively charged are useful for selectively staining the nuclei of dead cells, which usually have compromised cell membranes.

It is understood to one skilled in the art that cell membrane permeability of a dye is also affected by dye concentration and the size of the dye molecule. Thus, a relatively membrane impermeable dye may still be used to stain live cells by using a relatively high dye concentration, for example. Moreover, selectivity for staining dead cells in the presence of live cells may be made higher by using a dye that is highly positively charged and relatively large in size.

In various embodiments, anthraquinone dyes of Formula 1 that comprise primary, secondary or tertiary amino substituents are excellent for live cell staining while anthraquinone dyes of Formula 1 that comprise at least two substituents selected from amidino, guanidino, trialkylammonium and substituted derivatives thereof are preferred for selective staining of dead cells. In various embodiments, highly charged dyes are also preferred for staining fixed cells as well as fixed and permeabilized cells, which are commonly studied in immunofluorescence staining.

In one embodiment, Formula 1 comprises at least one enzyme substrate moiety wherein the transformation of the substrate moiety by an enzyme causes a detectable change in ether the spectral property or functionality of the anthraquinone dye. The transformation of the substrate moiety by the enzyme involves the cleavage of a chemical bond. Herein spectral properties mean the absorption and emission wavelengths and/or fluorescence quantum yield of the dye, and the functionality of the dye means the cellular binding target of the dye. In some case, a detectable functionality change means a cellular staining change from nonspecific cellular staining to a substantially nuclear specific staining. The detectable changes may be detected using any of the known means, such as a microscope, a flow cytometer, a microplate reader and the like.

Enzyme substrate moieties include those cleavable by peptidases, phosphatases, esterases, dealkylases, histone deacetylase (HDAC), β-galactosidase, and β-glucuronidase. The term "peptidase" will be used interchangeably with the term "protease", both being referred to as enzymes capable of cleaving a peptide bond. A peptidase may be an endopeptidase or exopeptidase. In general, at least one side of the said peptide bond is connected to a natural amino acid or amino acid residue. Preferably, when the substrate moiety is a substrate for a peptidase, the preferred peptidase is a caspase, a calpain, an endopeptidase and an elastase.

According to one embodiment, at least one of $R_1$ and $R_2$ and the oxygen atoms to which they are attached is a substrate moiety for an enzyme selected from the group consisting of an esterase, a phosphatase, a dealkylase, β-galactosidase, and β-glucuronidase. Enzymes such as these typically cleave an oxygen-carbon bond. In another embodiment, when at least one of $R_1$ and $R_2$ and the oxygen atoms to which they are attached is an enzyme substrate moiety, $R_3$ and $R_4$ do not comprise an enzyme substrate moiety. Examples of these embodiments are shown in Table 2.

According to another preferred embodiment, $R_1$ and $R_2$ are both H, acetyl, or acetoxymethyl (or AM), and at least one of $R_3$ and $R_4$ comprises an enzyme substrate moiety, which upon cleavage results in a nuclear binding anthraquinone dye. In general, the enzymatic cleavage is an event where $R_3$ or $R_4$ or a portion thereof that hinders nucleic acid binding is removed, thereby restoring or enhancing the functionality of the nucleic acid dye. In some cases, the enzymatically cleavable portion is a negatively charged moiety or a sterically bulky moiety. In some cases, such as that where substrate cleavage is by a peptidase or HDAC, the enzymatic process generates a positively charged amine group, which enhances nucleic acid binding of the dye. Some examples of preferred anthraquinone dyes comprising at least one enzyme substrate moiety are given in Table 2.

TABLE 2

List of anthraquinone dyes comprising an enzyme substrate moiety according to Formula 1

| Dye No. | Dye structure | Enzyme substrate moiety |
|---|---|---|
| 18 | | Benzyloxy for dealkylase |
| 19 | | Acetate for esterase |
| 20 | | AM ester for esterase |

TABLE 2-continued
List of anthraquinone dyes comprising an enzyme substrate moiety according to Formula 1
| Dye No. | Dye structure | Enzyme substrate moiety |
|---|---|---|
| 21 | 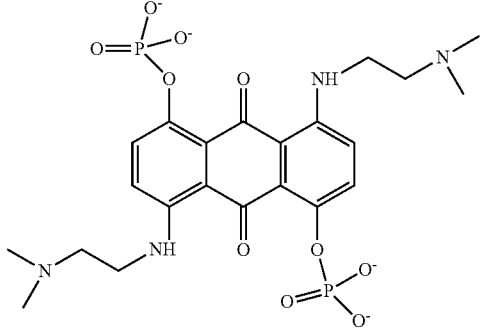 | Phosphate for phosphatase |
| 22 | 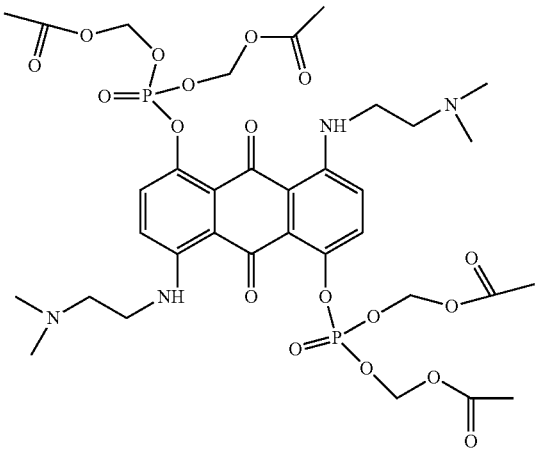 [SMILES: CC(=O)OCOP(=O)(OCOC(C)=O)Oc1ccc(NCCN(C)C)c2c1C(=O)c1c(NCCN(C)C)ccc(OP(=O)(OCOC(C)=O)OCOC(C)=O)c1C2=O] | Phosphate AM ester for esterase and phosphatase (double enzyme substrate moiety) |
| 23 | 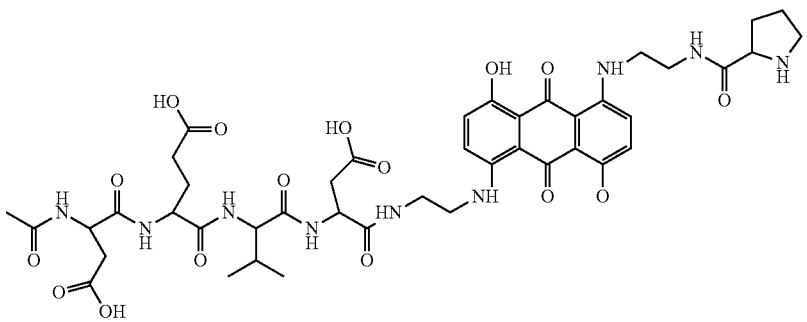 [SMILES: CC(=O)NC(CC(=O)O)C(=O)NC(CCC(=O)O)C(=O)NC(C(=O)NC(CC(=O)O)C(=O)NCCNc1ccc(O)c2c1C(=O)c1c(O)ccc(NCCNC(=O)C3CCCN3)c1C2=O)C(C)C] | Ac-DEVD peptide for caspase-3 |

TABLE 2-continued

List of anthraquinone dyes comprising an enzyme substrate moiety according to Formula 1

| Dye No. | Dye structure | Enzyme substrate moiety |
|---|---|---|
| 24 | 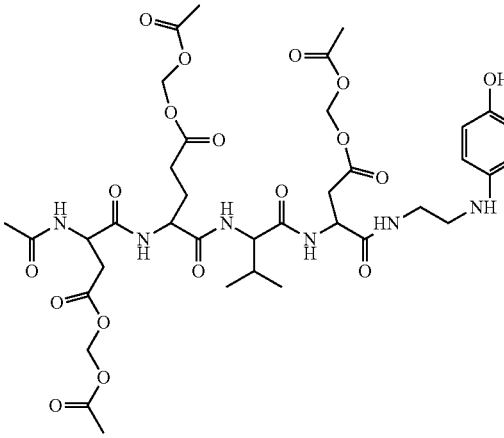 | Ac-DEVD AM ester peptide for esterase and caspase-3 (double enzyme substrate moiety) |

The present invention further discloses an anthraquinone dye comprising an enzyme substrate moiety according to the general structure of Formula 4:

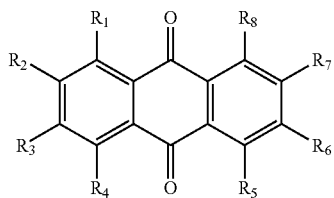

Formula 4 wherein at least one of $R_1$-$R_8$ is an enzyme substrate moiety or a substituent comprising an enzyme substrate moiety, wherein following the enzymatic event said substrate moiety or substituent comprising a substrate moiety results in a substituent selected from the group consisting of —OH, —$NH_2$, —NH-$L_3$-OH, and —NH-$L_3$-$NH_2$, where $L_3$ is a linker group.

In general, enzymatic processes that convert any of $R_1$-$R_8$ to —OH or —$NH_2$ cause a detectable change in the spectral property or the functionality of the dye. The spectral change may either be in absorption or fluorescence or both. In some cases, the enzymatic conversion of any of $R_1$-$R_8$ to —OH or —$NH_2$ also changes the functionality of the dye in addition to the spectral change. On the other hand, enzymatic conversion of any of $R_1$-$R_8$ to —NH-$L_3$-OH or —NH-$L_3$-$NH_2$ typically does not cause a spectral shift but mainly a change in the functionality of the dye.

In general, anthraquinone dyes comprising a hydroxy or primary amine are suitable as starting materials for making dyes comprising an enzyme substrate moiety according to Formula 4. In general, anthraquinone dyes having a hydroxy group are suitable for constructing dyes comprising a substrate moiety for a phosphatase, a dealkylase, an esterase, β-galactosidase or β-glucuronidase. Similarly, anthraquinone dyes having a primary amine group are suitable for constructing dyes comprising a substrate moiety for a peptidase, a histone deacetylase, or a similar enzyme capable of cleaving a peptide bond.

In various embodiments, said substrate moiety is a double substrate moiety, wherein the substrate moiety is initially a substrate for a first enzyme, which transforms the initial substrate moiety into a new substrate moiety for a second enzyme, which acts upon the new substrate moiety to cause a detectable change of the dye. Herein, the initial substrate moiety may be referred to as a "pro-substrate" for the subsequently generated second substrate moiety. Typically, the first enzyme that acts upon a double substrate moiety is an esterase and the second enzyme may be a peptidase, a phosphatase or oxidase. As an example, a double substrate moiety may be a peptide comprising one or more L-glutamic acid and/or L-aspartic acid residues, wherein the side chains of L-glutamic acid and/or aspartic acid are in the form of an ester, such as acetoxymethyl ester (i.e., AM ester). Because a peptide comprising acidic amino acids in an ester form can more easily cross cell membranes than does the peptide with the acidic amino acids existing as free acid form, anthraquinone dyes comprising such ester peptide substrate moiety may be suitable for live cell staining. Once the dye enters a cell, the ester peptide is first hydrolyzed to a peptide in its native form, which is subsequently cleaved by a peptidase that recognizes the peptide as its substrate, leading to a detectable change in the dye. As another example, a double substrate moiety may be a phosphate AM ester. An anthraquinone dye comprising such phosphate AM ester double substrate moiety can rapidly enter cells, where the phosphate AM ester is first hydrolyzed by an intracellular esterase to a phosphate substrate moiety, which is subsequently hydrolyzed or cleaved off by an intracellular phosphatase, leading to a detectable change of the dye.

Synthesis of Anthraquinone Dyes

There are many possible synthetic routes to the anthraquinone dyes according to the invention. The methods described below are only intended to be exemplary. Detailed procedures are further illustrated in the Examples section.

Syntheses of nuclear staining anthraquinone dyes according to Formula 1 may be carried out using method A or B. In method A, 1,5-dichloroanthraquinone is used as a key starting material, which is reacted either stepwise with two separate primary amines (i.e., $H_2NR_3$ and $H_2NR_4$) or in a single step with a large excess of one amine, $H_2NR_3$ or $H_2NR_4$, to form an amine-substituted anthraquinone intermediate. Stepwise amine substitution reaction permits the dye to be modified with two different substituents (i.e., —NHR$_3$ and —NHR$_4$) while single step substitution with a large excess of a single amine results in a symmetrically substituted anthraquinone dye. The amine substituted anthraquinone intermediate is subsequently oxidized to form the final product Amines suitable as H$_2$NR$_3$ or H$_2$NR$_4$ are either commercially available or can be readily prepared using methods known to one skilled in the art.

In method B, 1,5-diamino-4,8-dihydroxyanthraquinone is used as a key starting material, which is reacted with a R$_3$ or R$_4$ compound with an activated ester or acid chloride to form an amide linkage with the dye. Alternatively, 1,5-diamino-4, 8-dihydroxyanthraquinone is reacted via Michael addition reaction with a precursor R$_3$ or R$_4$ compound which comprises an α,β-unsaturated carbonyl, nitrile or similar moiety. The resulting intermediate product is further derivatized to a dye according to Formula 1 using known chemistries.

Synthesis of anthraquinone dyes comprising an enzyme substrate moiety typically starts with an anthraquinone dye comprising a hydroxy or a primary amino group. A phosphatase substrate moiety can be attached by reacting the hydroxy with phosphorous-oxytrichloride followed by hydrolysis. An esterase substrate moiety can be attached by reacting the hydroxy with an acid chloride, an anhydride or bromomethyl acetate, for example. Similarly, a dealkylase substrate moiety can be attached by reacting the hydroxy with an alkylating compound. To prepare anthraquinones comprising a peptidase substrate moiety, anthraquinones comprising a primary amine are reacted with an activated ester form of an amino acid or peptide. As needed, the amino acid or peptide may be in a protected form to avoid side reactions. Once the protected amino acid or peptide is attached to the dye, the intermediate may be deprotected using standard deprotection chemistry and then optionally further derivatized to form a double substrate moiety, for example.

Methods of Using Anthraquinone Dyes

The dyes of the invention are useful for analyzing cells, which may be dead, fixed or living. The cells may be in a suspension, adhered to a surface or associated with tissues. In general, anthraquinone dyes of the invention except for those that comprise an enzyme substrate moiety may be suitable for staining dead or fixed cells. Anthraquinone dyes of the invention that are substantially neutral, or that carry only weak acid groups (such as a carboxylic acid group) and/or weak basic groups (such as primary, secondary or tertiary amine groups) are preferred for staining live cells as these dyes tend to be more cell-membrane-permeable than dyes that are substantially positively charged under physiological condition. Substantially positively charged moieties under physiological condition include trialkylammonium, guanidino and amidino, for example.

The present invention provides a method of analyzing a biological sample comprising cells, comprising the steps of:
1) incubating said biological sample in a biological buffer in the presence of an anthraquinone dye of the invention for a time sufficient to cause staining;
2) illuminating the stained sample with a light source sufficient to excite the dye; and
3) detecting the emitted fluorescence from the sample using a suitable instrument.

In some cases, detection may be optionally made by measuring absorbance change. For example, in cases where an enzyme cleaves a substrate moiety off a dye of the invention to result in an aromatic hydroxy or amino group, a significant absorption color change may occur.

In one embodiment, dyes of the invention are used as nuclear counterstains. Nuclear counterstains are important tools for many fluorescence-based cell analyses, including but not limited to microscopy, flow cytometry and in-cell western analysis. In fluorescence microscopy, the specific marking of cell nuclei by a counterstain helps identify the locations of cells (particularly cells in tissues), count the number of cells, and serves as a reference relative to the staining of other cellular targets in multicolor imaging experiments. For example, in high-content screening (HCS) assays, a cell image acquisition-based cell analysis method widely used in drug screening, physical identification of cell nuclei is the first step prior to the evaluation of other cellular targets (Abraham et al., J. Biomol. Screen 13, 527 (2008)). Nuclear counterstains are also useful in flow cytometry and in in-cell western analysis to help measure DNA content and normalize cell numbers (Swerts et al., Clin. Chim Acta 379, 154 (2007); Chen et al., Hum Mol. Genet. 19(1): 196 (2010)).

Figure 2:
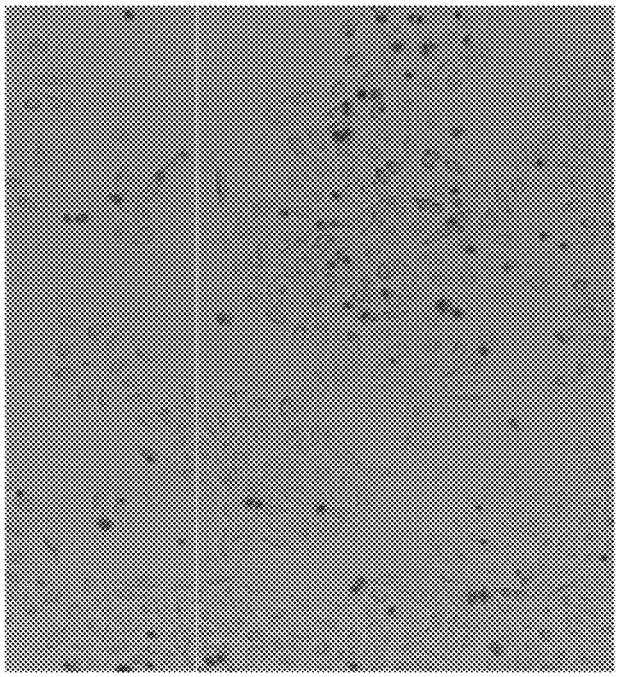
FIG. 2 shows toxicity approximately 18 hours after staining The figure shows bright-field microscopic images of HeLa cells stained with a) Draq5 (5 uM), and b) Dye No. 1 (20 uM), respectively, after 18 h. Dark spots are indicative of dead cells. The images show that cells stained with Draq5 resulted in more cell death than that with Dye No. 1.
Figure 2:
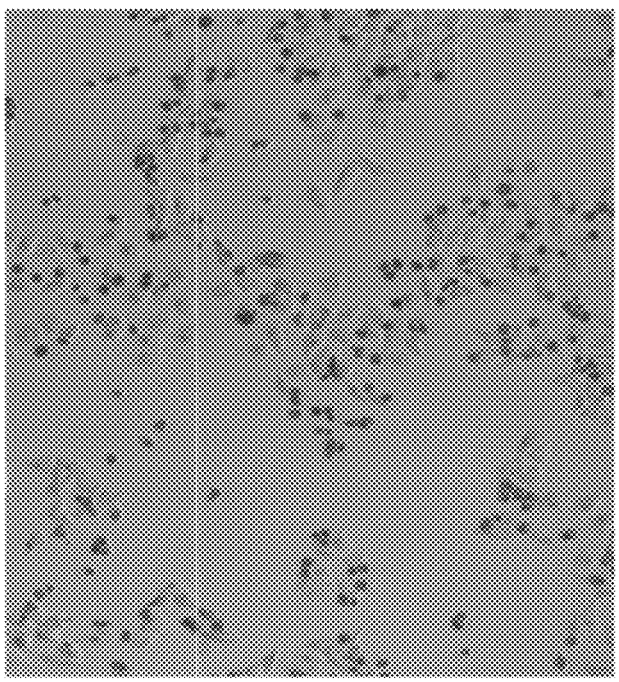

According to one embodiment, the biological sample comprises live cells, which may be in a form of cell suspension or tissue sample. To counterstain live cells, preferred anthraquinone dyes are those of Formula 1 that are readily cell-membrane-permeable. The membrane permeability of a dye is a relative term as it is a function of both the dye structure itself, the dye concentration and incubation temperature. Suitable cell membrane permeability can be readily determined by incubating live cells with different concentrations of dyes to be evaluated. According to one embodiment, a nuclear counterstain for live cells has a structure selected from Dye No. 1, Dye No. 3, Dye No. 4, Dye No. 6, Dye No. 10 and Dye No. 12. In various embodiments, a nuclear counterstain for live cells has the structure of Dye No. 1. An example of live cell staining by Dye No. 1 is shown in FIG. 1. As demonstrated, Dye No. 1 stained the nuclei of live cells specifically. However, an unexpected result is that Dye No. 1 is much less toxic than Draq5 as shown in FIG. 2. This advantage of Dye No. 1 is very important because the toxicity of Draq5 has been suggested to be a problem for its utility in certain live-cell assays designed for drug screening (Richard et al. Photochem. Photobiol. 87, 256 (2011)).

According to another embodiment, the sample comprises fixed cells or fixed and permeabilized cells. In immunofluorescence staining applications, cells are routinely fixed or fixed and permeabilized to facilitate antigen detection by fluorescently labeled antibodies. Since fixed and permeabilized cells have porous or compromised membranes, anthraquinone dyes of Formula 1 except those that comprise an enzyme substrate moiety may be suitable as nuclear counterstains.

Figure 3:
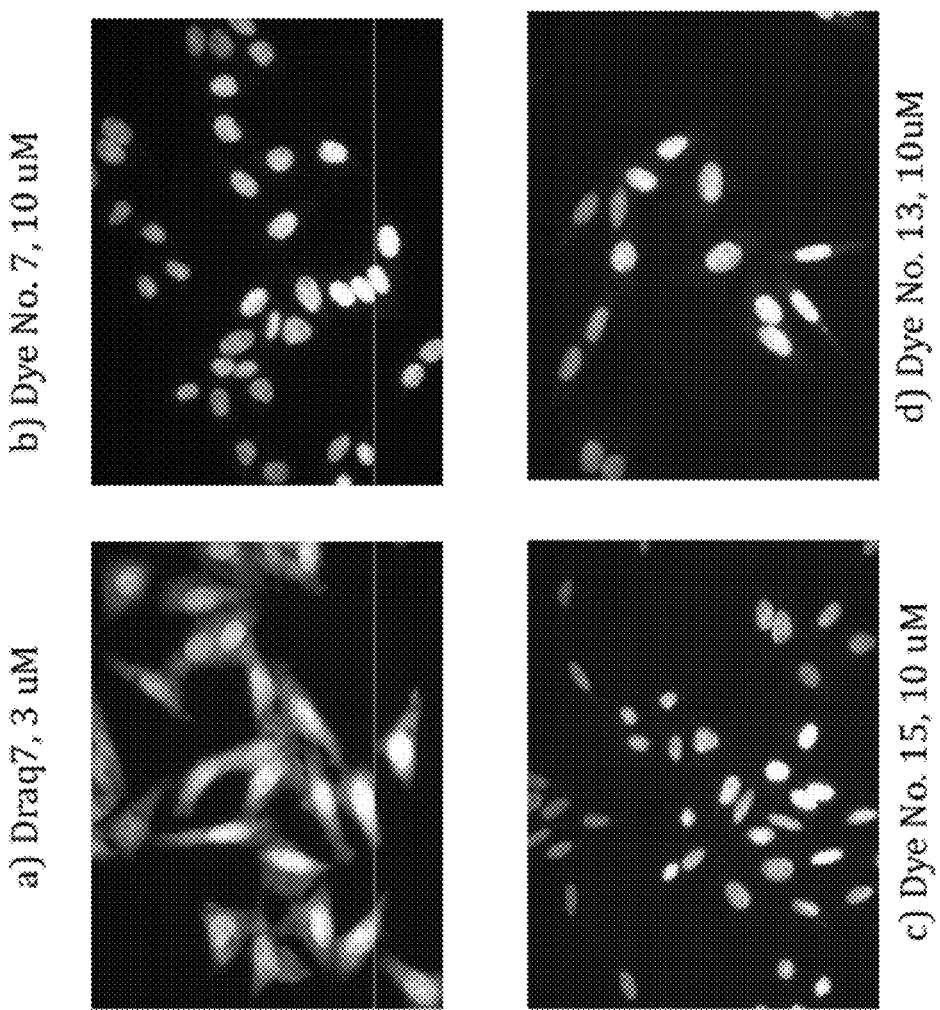
FIG. 3 shows staining of fixed and permeabilized cells. The figure shows fluorescence microscopic images of fixed and permeabilized HeLa cells stained with a) Draq7 (3 uM), b) Dye No. 7 (10 uM), c) Dye No. 15 (10 uM), and d) Dye No. 15 (10 uM), respectively. Anthraquinone dyes disclosed herein all stained cell nuclei specifically whereas Draq7 stained cell nuclei with high cytoplasmic background.
Figure 4:
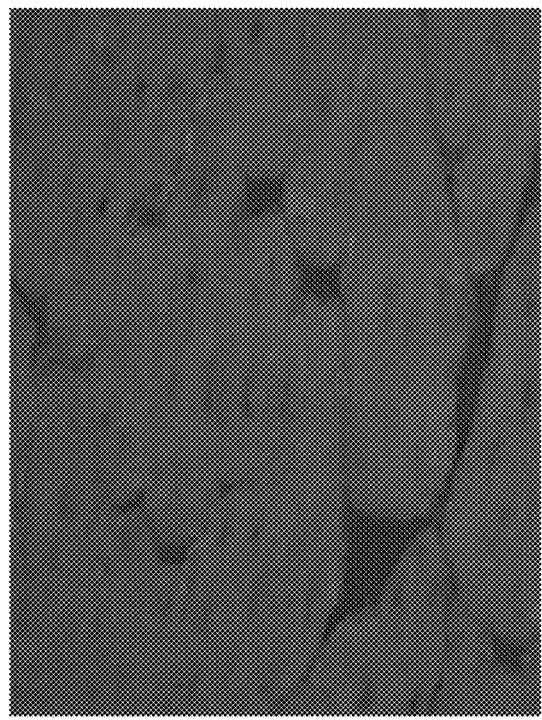
FIG. 4 shows acetone-fixed frozen sections of rat skeletal muscle, stained at 10 uM for five minutes at room temperature. The figure shows fluorescence microscopic image of rat skeletal muscle tissue stained with a) Dye No. 7, and b) Dye No. 7 plus $CF_{488}$A-phalloidin.
Figure 4:

According to one embodiment, preferred nuclear counterstains for fixed and permeabilized cells are those of Formula 1 that comprise at least two substituents selected from amidino, guanidino, trialkylammonium and substituted derivatives thereof. In various embodiments, counterstains for fixed and permeabilized cells are those anthraquinone dyes having the structures selected from Dye Nos. 6, 7, 9, 13, 15, 16 and 17. In various embodiments, the dyes are Dye Nos. 7, 13 and 15. Images of fixed and permeabilized cells stained with Dye Nos. 7, 13 and 15 and two commercial prior art nuclear counterstains Draq5 and Draq7 are shown in FIG. 3. Surprisingly, dyes according to the invention showed much better specificity for nuclear staining of fixed and permeabilized cells than Draq5 and Draq7. FIG. 4 shows that Dye No. 7 can also be used to stain tissues with excellent nuclear specificity.

Figure 5:
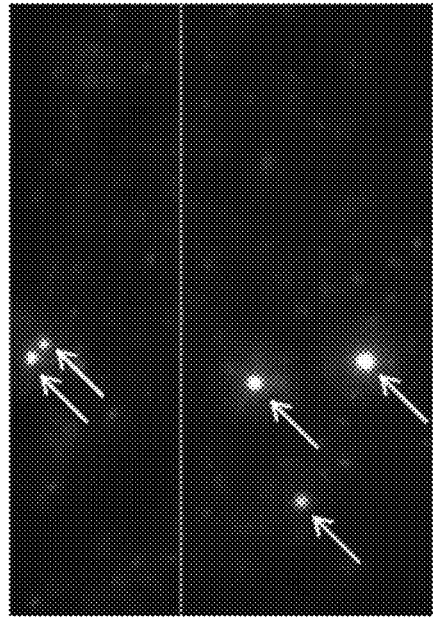
FIG. 5 shows selective staining of dead cells. The figure shows fluorescent microscopic images of a) live cell culture stained with cell-permeable Dye No. 1, and b) live-cell-impermeable Dye No. 7, respectively. Dye No. 1 stained all cells (HeLa cell nuclei), while Dye No. 7 selectively stained the nuclei of dead cells only (HeLa cells).
Figure 5:
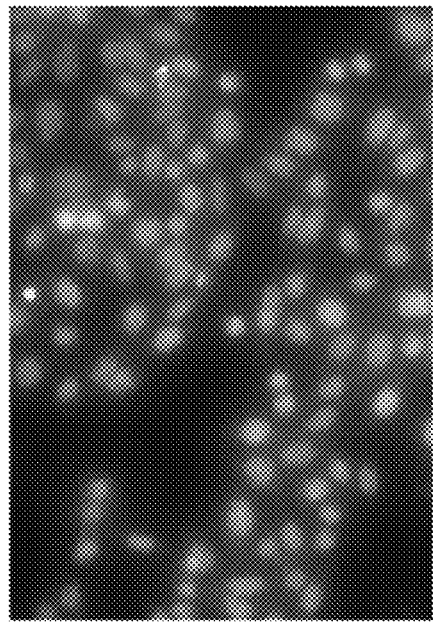

According to yet another embodiment of the invention, the biological sample comprises a mixture of healthy and dead cells, and the dye is an anthraquinone dye of Formula 1 that is cell-membrane impermeable. Use of such a cell impermeable dye provides a method of selectively staining dead cells in the presence of live cells. In one embodiment, the dye is Dye No. 7 or Dye No. 9. Preferably, the dye is Dye No. 9. According to one embodiment, the cell membrane impermeable anthraquinone dye is combined with another fluorescent probe selective for live cells. Such a staining method provides a way to detect the numbers of both live and dead cells in the same cell population. Commercial fluorescent probes that are designed to detect live cells only are available. For example, calcein AM is a probe that enters live cells and becomes hydrolyzed intracellularly by endogenous esterases in live cells to produce a green fluorescent dye. As another example, mitochondrial dyes that stain mitochondria in a membrane potential-dependent manner can be used to selectively stain live cells, which have healthy mitochondria. An example of Dye No. 7 selectively staining dead cells in the presence of live cells is shown in FIG. 5.

Detection of emitted fluorescence signals may be made with a variety of instruments including, but not limited to, microscopes, flow cytometers, plate readers and any variations thereof.

Figure 6:
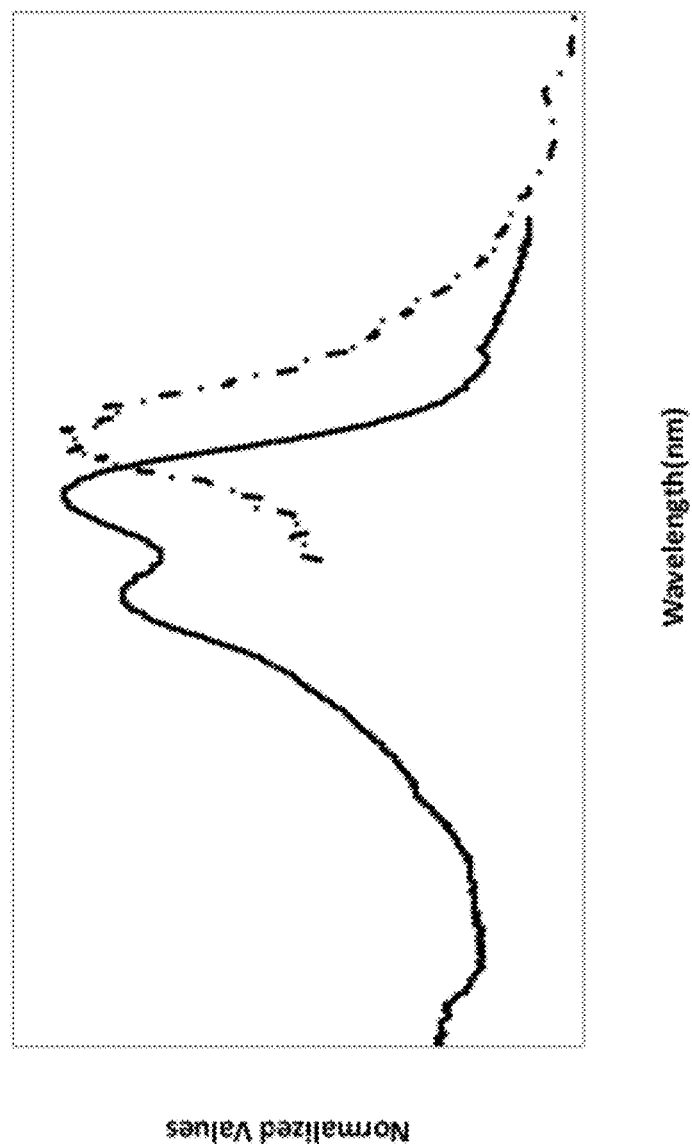
FIG. 6 shows absorption and emission spectra of Dye No. 7 (normalized values versus wavelength (nm)) in the presence of DNA.

At least some of the dyes of the invention are optimally excitable by red lasers having wavelength at 633, 635, 640 or 647 nm and are fluorescent at peak wavelength greater than 680 nm. The near infrared fluorescence emission of the dyes as counterstains is highly desirable as this leaves useful optical channels in the visible spectral region for the detections of other cellular targets by other cellular probes in multiparameter imaging analysis. For example, the near-IR fluorescent counterstains of the invention are ideal for use with the popular green fluorescent protein (GFP) or yellow fluorescent protein (YFP) in multicolor detections because of near complete spectral separation. The absorption and emission spectra of Dye No. 7 are shown in FIG. 6.

The present invention also provides a method for detecting enzyme activity, the method comprising the steps of:
1) incubating a biological sample comprising or thought to comprise an active enzyme in a biological buffer in the presence of an anthraquinone dye of Formula 1 or Formula 4 comprising an enzyme substrate moiety specific for said enzyme to be detected for at least 5 minutes;
2) illuminating the stained sample with a light source sufficient to excite the enzymatically produced dye product; and
3) detecting the emitted fluorescence from the sample using a suitable instrument.

The biological sample may be a suspension of live cells, live cells adhered to a surface, or a tissue sample comprising live cells. The sample may also be a living animal, where the dye is introduced by injection or other conventional delivery means associated with in vivo imaging.

Following a period of incubation, typically greater than about 5 minutes, more typically greater than about 15 minutes, any presence of an enzyme to which the substrate moiety is specific will transform the dye spectrally and/or functionally in a manner where the rate of transformation is proportional to the level of enzyme activity. Thus, the invention provides a convenient way to assay enzyme activity in live cells. Because certain enzyme activity may be associated with a disease and may be responsive to the presence of an externally applied agent, such as a drug candidate, the enzyme assay method of the present invention may be useful as a diagnostic tool for the disease and useful for drug screening. According to one preferred embodiment, said anthraquinone dye is enzymatically transformed from a non-nuclear staining dye to a nuclear staining dye.

In some embodiments, a dye of the invention comprising an enzyme substrate moiety may undergo change in the absorption spectrum of the dye following the enzymatic reaction. In such cases, the detection may also be made by following the absorbance change at an appropriate wavelength, such as at the absorption maximum wavelength of the starting dye or that of the reaction product.

Furthermore, the enzyme assay may be performed with an isolated enzyme and the detection may be made using a plate reader or a spectrophotometer.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Preparation of Compound No. 1

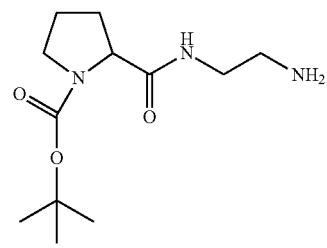

Compound No. 1

To a solution of BOC-L-Pro-OH (5 g, 23 mmol) in DMF (20 mL) at 0° C. was added Et$_3$N (3.2 mL, 23 mmol) and TSTU (7 g, 23 mmol). The mixture was stirred at 0° C. for 15 minutes and then added to a solution of ethylenediamine (3.1 mL, 46 mmol) in DMF (20 mL) at 0° C. The mixture was stirred at 0° C. for 30 minutes and then concentrated to dryness in vacuo. The residue was purified by column chromatography on silica gel to give an off-white oil (4.5 g).

Example 2

Preparation of Compound No. 2

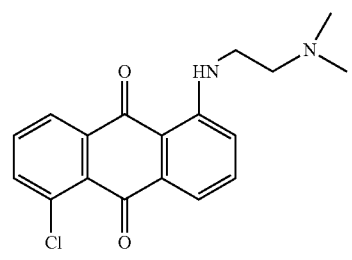

Compound No. 2

Compound No. 2 was prepared according to a literature procedure (Katzhendler et al., Eur. J. Med. Chem. 1989, 24, 23). A mixture of 1,5-dichloroanthraquinone (5 g, 18 mmol) and dimethylaminoethylenediamine (4 mL, 36 mmol) in toluene (200 mL) was refluxed for 3 days. The solvent was removed and the residue was purified by column chromatography on silica gel to give reddish-brown solid (2.5 g).

Example 3

Preparation of Compound No. 3

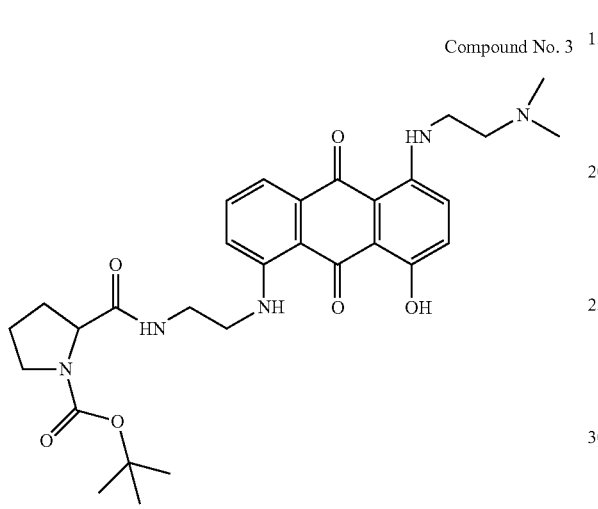

Compound No. 3

A mixture of Compound No. 2 (2.5 g, 7.6 mmol) and Compound No. 1 (4 g, 15.2 mmol) in dry toluene (50 mL) was refluxed for 3 days. The solvent was removed in vacuo and the solvent was purified by column chromatography on silica gel to give dark red solid (2 g).

Example 4

Preparation of Dye No. 1

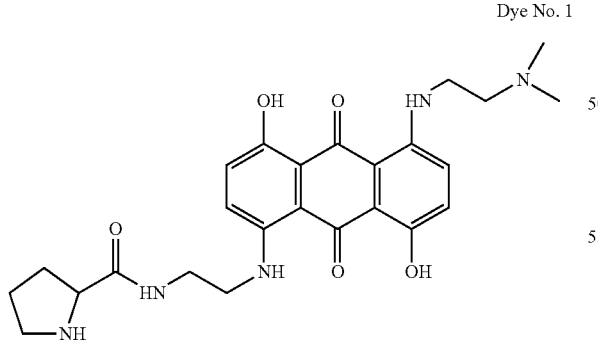

Dye No. 1

To a solution of Compound No. 3 (2 g, 3.6 mmol) in concentrated sulfuric acid (10 mL) at −10° C. was added portionwise sodium chlorate (1.5 g, 14.6 mmol) over a period of 1 hr. After the addition was completed, the temperature was allowed to warm up to room temperature and the mixture was stirred at room temperature for 2 hrs. The mixture was added dropwise to 1% NaHSO$_3$ (200 mL) and the solution was neutralized to pH=7 with 5N NaOH. The precipitate was collected by suction filtration and purified by preparative HPLC to give dark blue solid (100 mg).

Example 5

Preparation of Compound No. 4

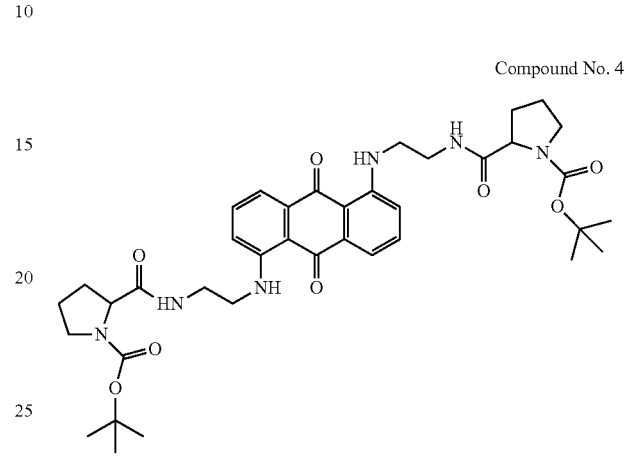

Compound No. 4

A mixture of 1,5-dichloroanthraquinone (1 g, 3.6 mmol) and Compound No. 1 (3 g, 11.6 mmol) in toluene (40 mL) was refluxed for 3 days. The solvent was removed and the residue was purified by column chromatography on silica gel to give dark red solid (0.4 g).

Example 6

Preparation of Dye No. 2

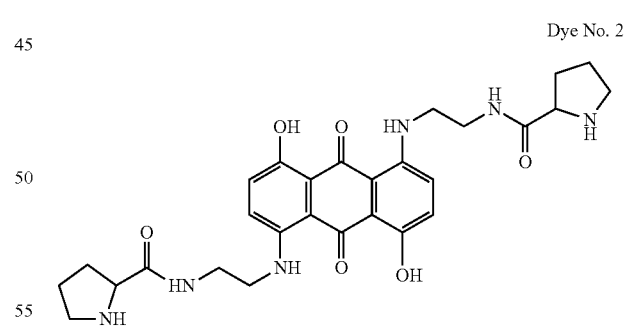

Dye No. 2

To a solution of Compound No. 4 (0.2 g, 0.28 mmol) in concentrated sulfuric acid (1 mL) at −10° C. was added portionwise of sodium chlorate (118 mg, 1.1 mmol) over a period of 15 minutes. After the addition was completed, the temperature was allowed to warm up to room temperature and the mixture was stirred at room temperature for 2 hrs. The mixture was added dropwise to 1% NaHSO$_3$ (15 mL) and the solution was neutralized to pH=7 with 5N NaOH. The aqueous layer was extracted with CHCl$_3$ (3×20 mL). The combined organic layers were dried with anhydrous Na$_2$SO$_4$ and

Example 7

Preparation of Compound No. 5

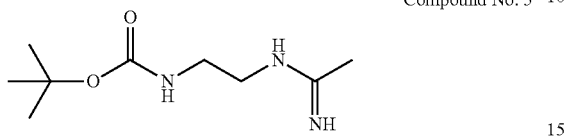

Compound No. 5

A solution of mono-t-BOC-ethylenediamine (2 g, 12.5 mmol)), ethyl acetimidate hydrochloride (4.6 g, 37.5 mmol) and diisopropylethylamine (10 mL, 62.5 mmol) in EtOH (100 mL) was heated at 100° C. in a sealed tube for 24 hrs. After cooling down to room temperature, the precipitate was collected by suction filtration and dried to a constant weight in vacuo to give white solid (1.8 g).

Example 8

Preparation of Compound No. 6

Compound No. 6

To a solution of Compound No. 5 (1.8 g, 9 mmol) in $CH_2Cl_2$ (20 mL) at 0° C. was added $CF_3CO_2H$ (5 mL). The solution was stirred at 0° C. for 2 hrs and concentrated to dryness in vacuo. $Et_2O$ (30 mL) was added and the suspension was stirred at room temperature overnight. The precipitate was collected by suction filtration and dried to a constant weight in vacuo (2.3 g).

Example 9

Preparation of Compound No. 7

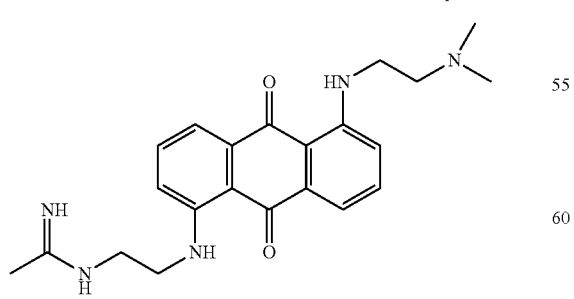

Compound No. 7

A mixture of Compound No. 2 (1 g, 3 mmol), Compound No. 6 (2 g, 6.1 mmol) and diisopropylethylamine (2 mL, 12.1 mmol) in DMSO (5 mL) was heated at 100° C. overnight. After cooling down to room temperature, the mixture was poured into water (50 mL). The precipitate was collected by suction filtration and dried to a constant weight in vacuo to give dark red solid (0.5 g).

Example 10

Preparation of Dye No. 3

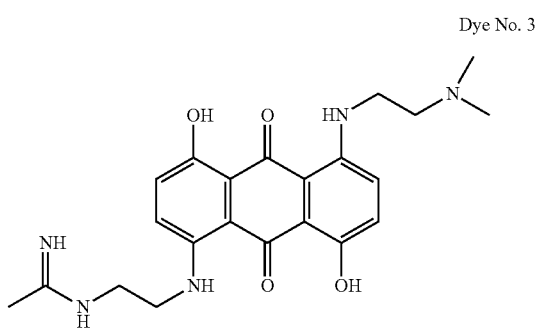 [SMILES: CC(=N)NCCNc1ccc(O)c2c1C(=O)c1c(O)ccc(NCCN(C)C)c1C2=O]

Dye No. 3

Dye No. 3 was prepared from Compound No. 7 (0.3 g, 0.77 mmol), sodium chlorate (0.32 g, 3.1 mmol) and concentrated sulfuric acid (3 mL) according to the procedure for synthesis of Dye No. 2. The crude dye was purified by preparative HPLC to give a dark blue solid (25 mg).

Example 11

Preparation of Compound No. 8

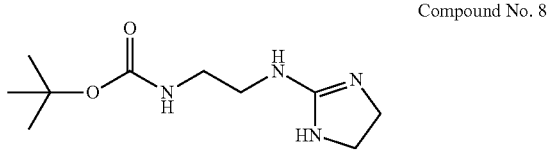 [SMILES: CC(C)(C)OC(=O)NCCNC1=NCCN1]

Compound No. 8

A solution of mono-tBOC-ethylenediamine (3 g, 18.6 mmol), 2-methylthio-2-imidazoline hydroiodide (6.6 g, 56.3 mmol) and diisopropylethylamine (15 mL, 93 mmol) in EtOH (150 mL) was heated at 100° C. in a sealed tube for 24 hrs. After cooling down to room temperature, the precipitate was collected by suction filtration and dried to a constant weight in vacuo to give white solid (3.2 g).

Example 12

Preparation of Compound No. 9

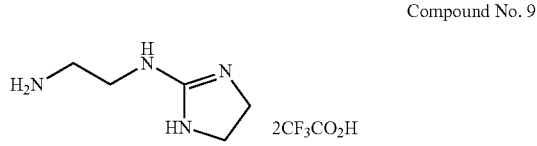

Compound No. 9

Compound No. 9 (3 g) was prepared from Compound No. 8 (3.2 g, 14 mmol) according to the synthesis of Compound No. 6.

Example 13

Preparation of Compound No. 10

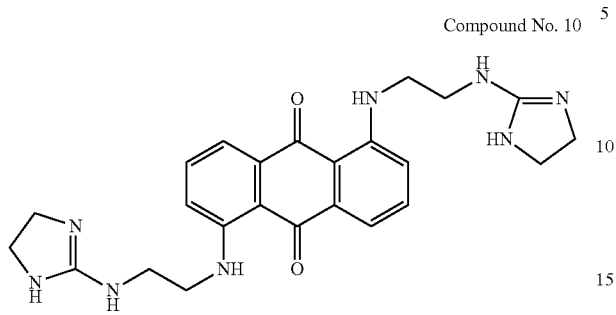

Compound No. 10

A mixture of 1,5-dichloroanthraquinone (0.6 g, 2.1 mmol), Compound No. 9 (3 g, 8.4 mmol) and diisopropylethylamine (1.5 mL, 9.2 mmol) in DMSO (10 mL) was heated at 100° C. overnight. After cooling down to room temperature, the mixture was poured into water (100 mL). The precipitate was collected by suction filtration and purified by preparative HPLC to give dark red solid (0.8 g).

Example 14

Preparation of Dye No. 13

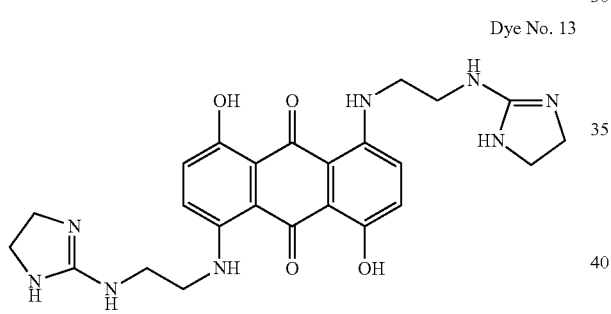

Dye No. 13

Compound No. 13 (80 mg) was prepared from Compound No. 10 (0.7 g, 1.5 mmol) according to the synthesis of Dye No. 3.

Example 15

Preparation of Compound No. 11

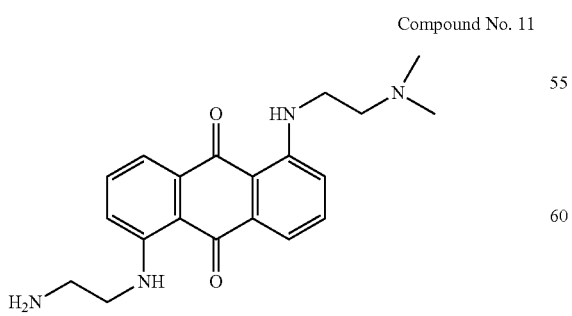

Compound No. 11

Compound No. 11 was prepared according to the literature method (Katzhendler et al., Eur. J. Med. Chem. 1989, 24, 23).

Example 16

Preparation of Compound No. 12

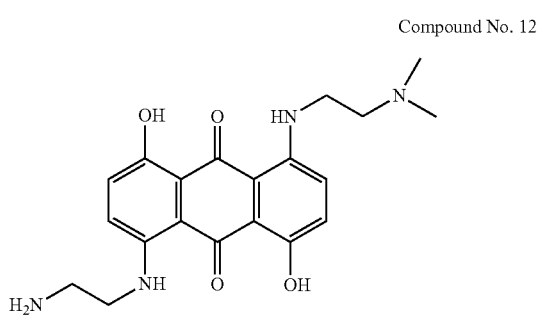 [SMILES: CN(C)CCNc1ccc(O)c2c1C(=O)c1c(O)ccc(NCCN)c1C2=O]

Compound No. 12

Compound No. 12 (0.12 g) was prepared from Compound No. 11 (0.7 g, 2 mmol) according to the synthesis of Dye No. 3.

Example 17

Preparation of Dye No. 5

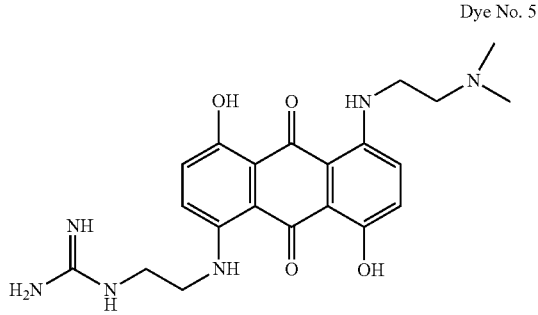 [SMILES: CN(C)CCNc1ccc(O)c2c1C(=O)c1c(O)ccc(NCCNC(=N)N)c1C2=O]

Dye No. 5

A mixture of Compound No. 12 (0.1 g, 0.26 mmol), S-methylisothiourea hemisulfate salt (0.1 g, 0.78 mmol) and diisopropylethylamine (0.7 mL, 4.3 mmol) in EtOH (10 mL) was heated at 100° C. in a pressure tube for 24 hrs. After cooling to room temperature, the mixture was concentrated to dryness in vacuo and the residue was purified by preparative HPLC to give a dark blue solid (11 mg).

Example 18

Preparation of Dye No. 7

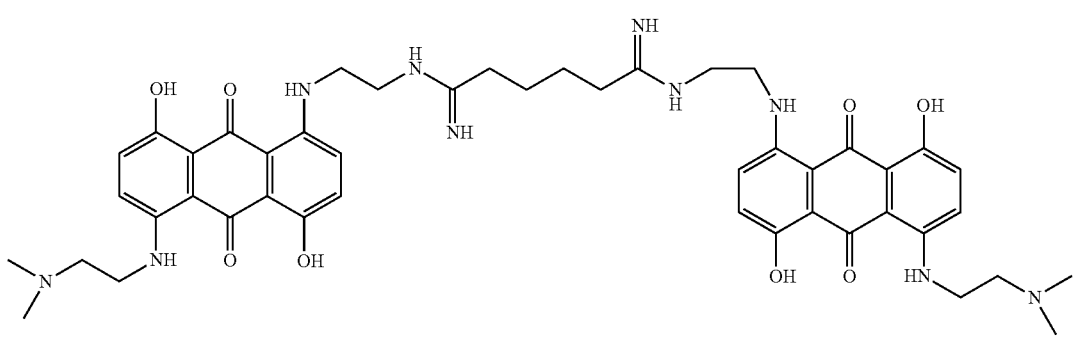

Dye No. 7

A mixture of Compound No. 12 (20 mg, 0.05 mmol), dimethyl adipimidate dihydrochloride (6.2 mg, 0.025 mmol) and diisopropylethylamine (87 uL, 0.5 mmol) in EtOH (1 mL) was heated at 70° C. overnight. After cooling down to room temperature, the mixture was concentrated to dryness in vacuo. The residue was stirred as a suspension in CH$_3$CN and the dark blue precipitate (3 mg) was collected by suction filtration.

Example 19

Preparation of Compound No. 13

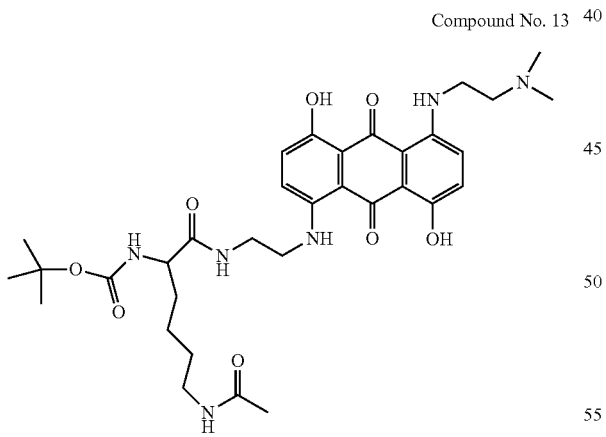

Compound No. 13

To a solution of BOC-L-Lys(Ac)-OH (22.5 mg, 0.08 mmol) in DMF (0.5 mL) was added diisopropylethylamine (36 uL, 0.2 mmol) and TSTU (23.5 mg, 0.8 mmol). The mixture was stirred at room temperature for 30 minutes that was followed by the addition of Compound No. 12 (10 mg, 0.026 mmol). After stirring at room temperature for 2 hrs, the solution was concentrated to dryness in vacuo and the residue was stirred as a suspension in CH$_3$CN (0.5 mL) and EtOAc (0.5 mL) at room temperature overnight. The dark blue precipitate (2 mg) was collected by suction filtration and dried to a constant weight. Compound No. 13 serves as a HDAC substrate.

Example 20

Preparation of Compound No. 14

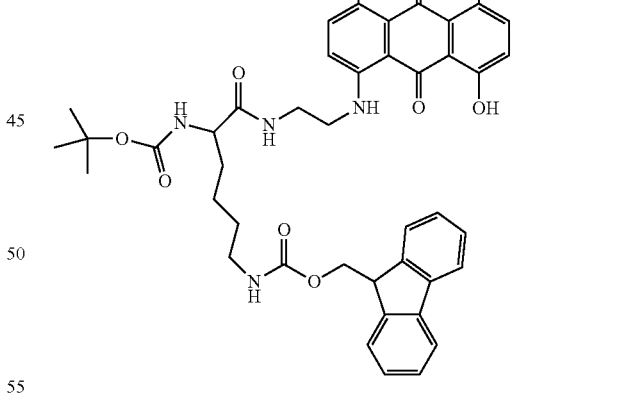

Compound No. 14

To a solution of BOC-Lys(FMOC)-OH (24.4 mg, 0.05 mmol) in DMF (0.5 mL) was added diisopropylethylamine (36 uL, 0.2 mmol) and TSTU (17 mg, 0.056 mmol). The mixture was stirred at room temperature for 30 minutes that was followed by the addition of Compound No. 12 (10 mg, 0.026 mmol). After stirring at room temperature for 2 hrs, the solution was concentrated to dryness in vacuo and the residue was stirred as a suspension in Et$_2$O (1 mL) and EtOAc (0.5 mL) at room temperature overnight. The dark blue precipitate (5 mg) was collected by suction filtration and dried to a constant weight.

Example 21

Preparation of Compound No. 15

Compound No. 15

To a solution of Compound No. 14 (5 mg, 0.006 mmol) in MeOH (1 mL) was added piperidine (10 uL) and the mixture was stirred at room temperature overnight. The mixture was concentrated to dryness in vacuo and stirred as a suspension in Et$_2$O (1 mL) and EtOAc (0.3 mL). The dark blue precipitate (2 mg) was collected by suction filtration.

Example 22

Preparation of Compound No. 16

Compound No. 16

Compound No. 16 (6 mg) was prepared from Compound No. 12 (10 mg, 0.026 mmol) and BOC-L-Asp(OBut)-OH (20 mg, 0.007 mmol) according to the synthesis of Compound No. 14.

Example 23

Preparation of Compound No. 17

Compound No. 17

To a suspension of Compound No. 16 (5 mg, 0.008 mmol) in CH$_2$Cl$_2$ (0.35 mL) at room temperature was added TFA (0.35 mL). The mixture was stirred at room temperature overnight and the residue was stirred as a suspension in EtOAc (0.5 mL) and Et$_2$O (0.5 mL). The dark blue precipitate (2 mg) was collected by suction filtration. This is an example of a substrate for Caspases 3 and 7.

Example 24

Preparation of Compound No. 18

Compound No. 18

To DRAQ5 (100 ug, Biostatus Ltd) in DMF (0.1 mL) at 0° C. was added diisopropylethylamine (3 uL) and bromomethyl acetate (2 uL). The mixture was stirred at 0° C. for 1 hr and then at room temperature overnight. The solution was concentrated to dryness in vacuo and the residue was stirred as a suspension in EtOAc (150 uL) and CH$_3$CN (50 uL) at room temperature for 6 hrs. The dark blue precipitate (90 ug) was collected by suction filtration. This compound is an example of an esterase substrate.

Example 25

Preparation of Compound No. 19

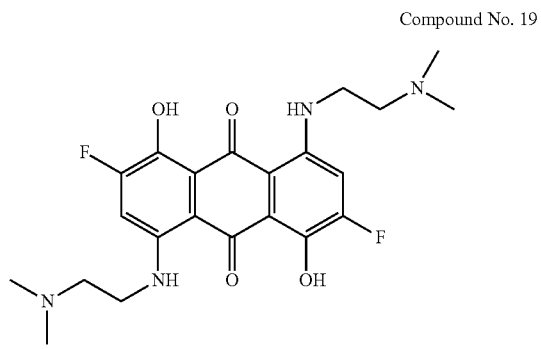

Compound No. 19

To a solution of DRAQ5 (100 ug) in water (100 uL) at 0° C. was added Selectfluor (100 ug). The mixture was stirred at room temperature for 5 hrs and then concentrated to dryness in vacuo. The residue was stirred as a suspension in $CH_3CN$ (200 uL) and the dark blue solid (50 ug) was collected by suction filtration.

Example 26

Preparation of Dye No. 25

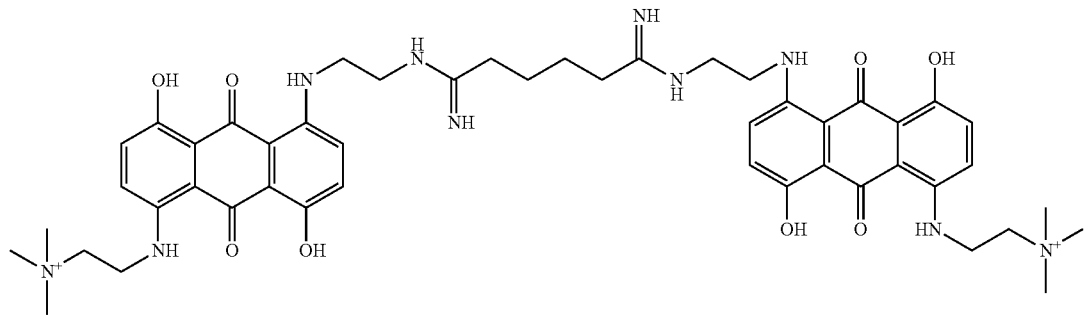

Dye No. 25 was prepared from Dye No. 7 (prepared as described in Example 18) by incubating with a 20-fold excess of methyl iodide in a sealed tube at 60° C. for 24 hours. The iodide salt of Dye No. 25 was obtained.

Example 27

Staining Live Cells with Dye No. 1

Live, adherent HeLa cells grown in 12-well plates were treated with either 5 μM DRAQ5 or 10 μM of Dye No. 1 in 1× phosphate buffered saline (PBS). Cells were incubated at 37° C. for 5 minutes. Fluorescence was observed using an epifluorescence microscope with the CY5 filter. The results show Dye No. 1 and Draq5 both stained the nuclei of live cells with high specificity at their respective optimal dye concentrations (FIG. 1).

Example 28

Toxicity of DRAQ5 and Dye No. 1

Live HeLa cells were treated with either 5 μM DRAQ5 or 20 μM Dye No. 1 in 1×PBS for 5 minutes at 37° C. The dye/PBS solution was removed and replaced with fresh Dulbecco/Vogt modified Eagle's minimal essential medium (DMEM) supplemented with bovine growth serum (BGS). The cells were incubated at 37° C. for approximately 18 hours, and observed under bright-field at 10× magnification (FIG. 2). The results show that Dye No. 1 of the invention caused fewer cell deaths than Draq5 even at a much higher concentration than the latter.

Example 29

Staining of Fixed and Permeabilized Cells

Adherent HeLa cells in 12-well plates were fixed with 4% paraformaldehyde for 15 minutes at room temperature. Cells were then permeabilized with 0.5% Triton X-100 for 10 minutes at room temperature. Three micromolar (3 μM, the manufacturer's recommended concentration) DRAQ7 or 10 μM Dye No. 7, 13, or 15 were added to the fixed and permeabilized cells in 1×PBS and incubated for 5 minutes at room temperature. The dye/PBS solution was removed and replaced with fresh 1×PBS. Fluorescence was observed using an epifluorescence microscope with the CY5 filter (FIG. 3).

The results show that dyes of the invention are much more specific in nuclear staining than Draq7 at their respective optimal dye concentrations.

Example 30

Staining of Tissue Sections with Dye No. 7

Acetone-fixed frozen sections of rat skeletal muscle were purchased from Biochain Institute Inc. (Hayward, Calif.). Sections were rinsed in phosphate buffered saline and stained with 10 uM Dye No. 7 and 5 units/mL CF488A-phalloidin (Biotium Inc, Hayward, Calif.) for five minutes at room temperature. Sections were rinsed twice in phosphate buffered saline and mounted with EverBrite mounting medium (Biotium, Inc, Hayward, Calif.). Tissue fluorescence was imaged using the FITC and Cy5 filter sets of an Olympus IX71 epifluorescence microscope and a Q-Imaging Retiga 2000R Fast 1394 mono camera (FIG. 4).

Example 31

Staining of Live (Unfixed) HeLa Cultures with Dye No. 1(Live-Cell-Permeable Nucleic Acid Dye) or Dye No. 7(Live-Cell-Impermeable Nucleic Acid Dye)

HeLa cells were seeded at a density of 2×10$^4$ cells in 100 uL culture medium per well in tissue culture treated, optical bottom, black 96-well plates. One day after seeding, 1 uL of 500 uM dye stock in DMSO was added directly to the culture medium (100 uL) and mixed by trituration. The cells were incubated at room temperature for five minutes. The culture medium containing dye was removed and replaced by 100 uL phosphate buffered saline. Cellular fluorescence was imaged using an the Cy5 filter set of an Olympus IX71 epifluorescence microscope and a Q-Imaging Retiga 2000R Fast 1394 mono camera (FIG. 5). The results show that the cell membrane permeable dye Dye No. 1 stained the nuclei of all cells whereas the cell membrane impermeable dye Dye No. 7 selectively stained the nuclei of dead cells only. Probes that can selectively detect dead cells are useful in cell viability assays, which are widely practiced in drug screening.

Example 32

Absorption and Emission Spectra of Dye No. 7 in the Presence of DNA

The absorption spectrum of Dye No. 7 (1 uM) in the presence of 40 ug/mL calf thymus DNA was measured on a Badmen Coulter DU-800 spectrophotometer. The fluorescence emission spectrum of the same solution was measured on a Hitachi F-4500 fluorescence spectrophotometer. The absorption spectrum shows that the dye is excitable by common laser lines at 633, 635, 640 and 647 nm. The fluorescence emission in the far-red to near-IR region makes the dye ideal for multicolor imaging experiments where green, yellow and orange colored probes are also used. FIG. 6.

Example 33

Normalizing or Counting Cell Number Using Dyes of the Invention

Figure 7:
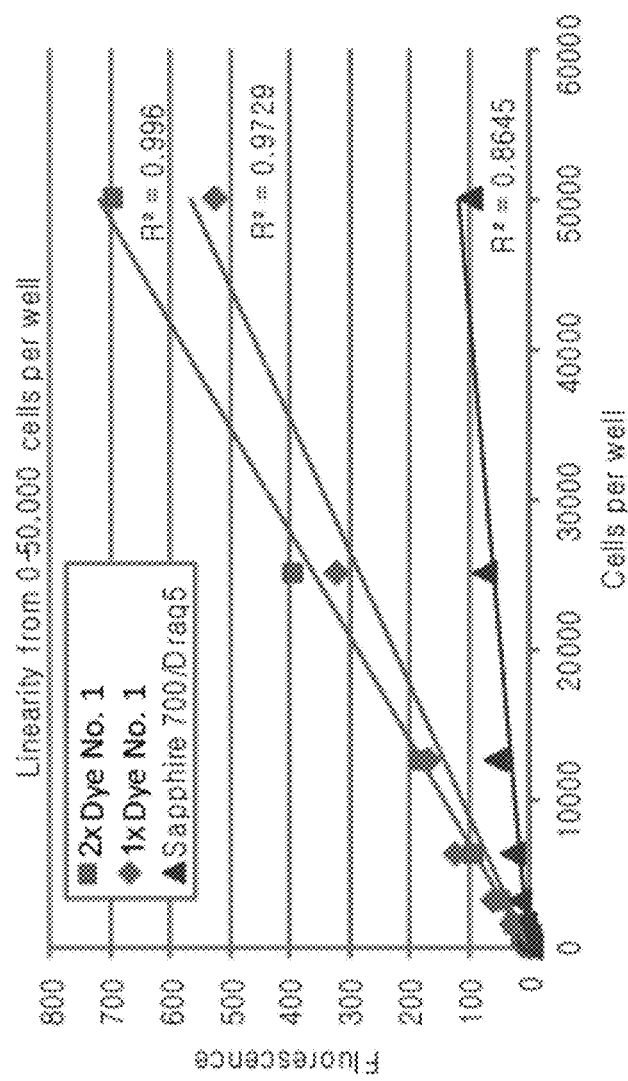
FIG. 7 shows the results of a cell counting experiment using Dye No. 1. Observed fluorescence was linear with the number of cells stained.

HeLa cells were counted/normalized using Dye No. 1. HeLa cells were seeded in 96-well-lates at several densities per well (as indicated on the x-axis of FIG. 7). After 24 hours, cells were fixed, permeabilized, and stained with the indicated dyes for one hour at room temperature according to the protocol provided by the supplier of the DRAQ5/Sapphire700 system. Fluorescence was quantitated using a LI-COR Odyssey system. HeLa cells seeded at 25,000 cells were confluent at the time of the assay. Results are shown in FIG. 7.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A substituted anthraquinone dye of Formula 5:

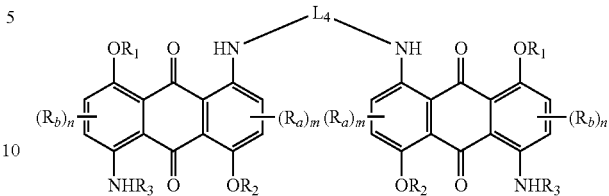

wherein:
each $R_a$ and $R_b$ is independently H, methyl, methoxy or a halogen;
each m and n is independently 0, 1, or 2;
$R_1$ and $R_2$ are H;
each $R_3$ is independently H, methyl, formyl, acetyl, an alkanoyl having the formula of Formula 2, or an alkyl having the formula of Formula 3:

Formula 2

Formula 3

$L_1$ is a link comprising 2-12 atoms selected from C, N, and O;
$X_1$ is a substituent selected from the group consisting of a substituted or unsubstituted amino, a substituted or unsubstituted amidino, a substituted or unsubstituted guanidino, a substituted or unsubstituted aminooxy, a substituted or unsubstituted hydroxylamino, a substituted or unsubstituted hydrazino, a $C_{3-6}$ trialkylammonium, a substituted or unsubstituted, natural or unnatural amino acid with a free alpha- or beta-amine where the amino acid is attached to $L_1$ via an amide bond;
$L_2$ is a link comprising 2-12 atoms selected from C, N, and O;
$X_2$ is selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid where the amino acid is attached to $L_2$ via an amide bond; or $X_2$ is a mono-, di- or trisubstituted amino group;
$L_4$ is -$L_2$-$X_2'$-$L_2'$-$X_2''$-$L_2''$-, wherein $L_2$, $L_2'$, and $L_2''$ are independently links comprising 2-12 atoms selected from C, N, and O; and
$X_2'$ and $X_2''$ are independently selected from the group consisting of a substituted or unsubstituted amidino, a substituted or unsubstituted guanidino, a substituted or unsubstituted aminooxy, a substituted or unsubstituted hydroxylamino, a substituted or unsubstituted hydrazino, a substituted or unsubstituted, natural or unnatural amino acid with a free alpha- or beta-amine where the amino acid is attached to $L_2$ via an amide bond; or $X_2$ is a mono-, di- or trisubstituted amino group.

2. A substituted anthraquinone dye according to claim 1, wherein each $L_2$, $L_2'$, and $L_2''$ of $L_4$ is independently $C_2$-$C_{12}$ alkylene, for example methylene or ethylene.

3. A substituted anthraquinone dye according to claim 1, wherein $L_2$ and $L_2''$ of $L_4$ are ethylene.

4. A substituted anthraquinone dye according to claim 1, wherein $X_2'$ and $X_2''$ are amidino.

5. A substituted anthraquinone dye according to claim 1, wherein the dye has the Formula:

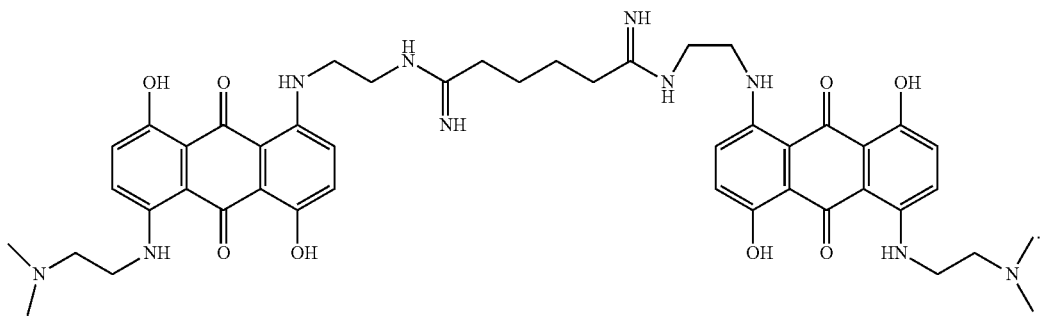

6. A substituted anthraquinone dye according to claim 1, wherein the dye has the Formula:

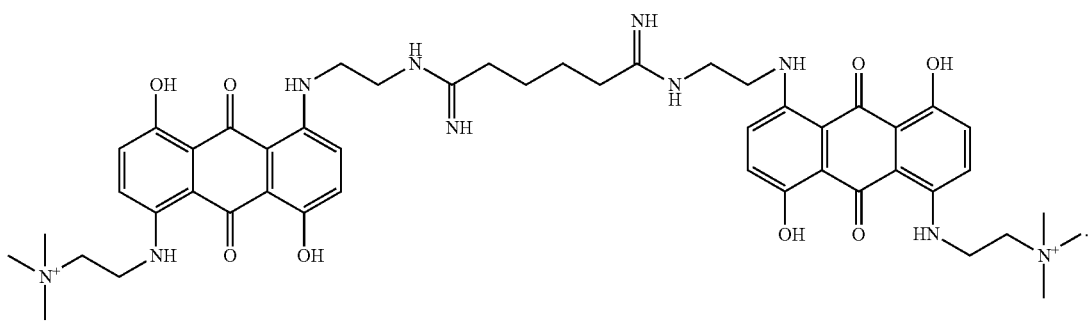

7. A substituted anthraquinone dye according to any preceding claim, wherein $R_a$ and $R_b$ are both H and $n=m=2$.

* * * * *